United States Patent [19]
Roberts et al.

[11] Patent Number: 5,357,041
[45] Date of Patent: Oct. 18, 1994

[54] HEPARIN- AND SULFATIDE-BINDING PEPTIDES FROM THE TYPE I REPEATS OF HUMAN THROMBOSPONDIN

[75] Inventors: David D. Roberts, Bethesda; Nenghua Guo, Chevy Chase; Henry C. Krutzsch, Bethesda, all of Md.

[73] Assignee: The United States of America as represented by the Secretary of the Department of Health and Human Services, Washington, D.C.

[21] Appl. No.: 801,812

[22] Filed: Dec. 6, 1991

[51] Int. Cl.$^5$ .................... A61K 37/00; A61K 37/02; C07K 5/00; C07K 7/00
[52] U.S. Cl. .................................. 530/326; 530/327; 530/328; 530/329; 530/330
[58] Field of Search ............... 530/324, 326, 327, 328, 530/329, 330; 514/12, 13, 14, 15, 16, 17, 18

[56] References Cited

FOREIGN PATENT DOCUMENTS 0443404  8/1991  European Pat. Off. .
WO90/01496  2/1990  PCT Int'l Appl. .

OTHER PUBLICATIONS

Prater et al., *J. Cell Biol.*, vol. 112, pp. 1031–1040, (1991).
Roberts et al., *J. Biol. Chem.*, vol. 260, No. 16, pp. 9405–9411, 5 Aug. 1985.
Bornstein et al., *J. Biol. Chem*, vol. 266, No. 20, pp. 12821–12824, 15 Jul. 1991.
Tuszynski, George P., et al. "Biological Activities of Peptides and Peptide Analogues Derived from Common Sequences Present in Thrombospondin, Properdin, and Malarial Proteins", *J. Cell Biology*, vol. 116, No. 1, (Jan. 1992) pp. 209–218.
Guo, Neng-hua, et al. "Heparin- and Sulfatide-binding Peptides from the Type I Repeats of Human Thrombospondin Promote Melanoma Cell Adhesion", *Proc. Natl. Acad. Sci.*, vol. 89, No. 7, (Apr. 1, 1992) pp. 3040–3044.
Guo, Neng-hua, et al. "Heparin-binding Peptides from the Type I Repeats of Thrombospondin: Structural Requirements for Heparin Binding and Promotion of Melanoma Cell Adhesion and Chemotaxis", *J. Biol. Chem.*, vol. 267, No. 27, (Sep. 25, 1992) pp. 19349–19355.
Cardin et al, Arteriosclerosis, vol. 9, pp. 21–32 (1989).
Rich et al, Science, vol. 249:1574–1577, (1990).
Prater et al, J. Cell Biol. vol. 112, pp. 1031–1040 (1991).
Zabrenetzky et al, Cancer Res., vol. 50, pp. 5937–5942 (1990).
Roberts et al, J. Biol. Chem. 260, 9405–9411 (1985).
Funahashi et al, Anal, Biochem. 126, 414–421 (1982).
Danilov et al, Exp. Cell Res. 182, 186–196 (1989).
Todaro et al, Proc. Natl. Acad. Sci USA 77, 5258–5262 (1980).
Roberts et al, J. Cell Biol. 104, 131–139 (1987).
Taroboletti et al, J. Biol. Chem. 265, 12253–12258 (1990).
Bornstein et al, J. Biol. Chem. 266, 12821–12824 (1991).
Jackson et al, Physiol. Rev. 71, 481–539, (1991).
Blackburn et al, J. Biol. Chem. 259, 939–941 (1984).
Cygler et al, Science 252, 442–445 (1991).
Sturgeon et al, Carbohydr. Res. 103, 213–219 (1982).
Holt et al, J. Biol. Chem. 264, 12138–12140 (1989).
Roberts, Cancer Res. 48, 6785–6792 (1988).
Kaesberg et al, J. Clin. Invest. 83, 994–1001 (1989).

*Primary Examiner*—Merrell C. Cashion, Jr.
*Assistant Examiner*—A. M. Davenport
*Attorney, Agent, or Firm*—Lowe, Price, LeBlanc & Becker

[57] ABSTRACT

The present invention relates to peptides from the three type I repeats of human endothelial cell thrombospondin, which bind to sulfated glycoconjugates including heparin and sulfatide. Such peptides are useful in glycoconjugate binding pharmaceutical compositions and in a method for binding glycoconjugates in a subject.

9 Claims, 12 Drawing Sheets

HEPARIN- AND SULFATIDE-BINDING PEPTIDES FROM THE TYPE I REPEATS OF HUMAN THROMBOSPONDIN

TECHNICAL FIELD

The present invention relates to peptides from the three type I repeats of human endothelial cell thrombospondin, which binds to sulfated glycoconjugates including heparin and sulfatide.

BACKGROUND OF THE INVENTION

Heparin binding is critical for activities in many cellular growth factors, cell adhesion molecules, and certain enzymes involved in the blood clotting cascade. Agents to inhibit these interactions have found numerous uses in prevention of thrombosis. Heparin analogues have been shown to have anti-tumor and antimetastatic activities.

Peptides that bind to heparin have been identified or isolated from many heparin binding proteins (see, for example Cardin et al, Arteriosclerosis, Vol. 9, pages 21–32 (1989)). Examples of heparin binding peptides identified from adhesion molecules include type IV collagen, laminin, and fibronectin. All have clusters of basic amino acids which fit consensus sequences defined by comparison of many heparin binding proteins (see Cardin et al, as above). The binding constants of the Cardin et al peptides and other peptide described in this art area are in the general range of $10^4$ to $10^3$ molar$^{-1}$.

Peptides from malaria circumsporozoite protein have been disclosed to mediate cell adhesion (Rich et al, Science, Vol 249:1574–1577, (1990)). Such peptides suffer from the disadvantages of not binding heparin and the adhesion activity was ascribed to a sequence Val-Thr-Cys-Gly, which is inactive for heparin binding.

Peptides from thrombospondin have been disclosed (Prater et al, J. Cell Biol. Vol 112, pages 1031–1040 (1992)). The sequences of Prater have a significant disadvantage since they are insufficient to bind to heparin or related sulfated glycoconjugates with high affinity.

Accordingly, there is a need in the present art for highly potent peptides that will bind to heparin or related sulfated glycoconjugates with high affinity. There is particularly a need for such peptides which are also useful to prevent interaction of heparin or related sulfated glycoconjugates with adhesion molecules, growth factors, cells or heparin-dependent enzymes.

OBJECT OF THE INVENTION

Accordingly, it is an object of the present invention to overcome the difficulties in the prior art as described above.

It is a further object of the present invention to provide highly potent peptides having sequences which bind to heparin or related sulfated glycoconjugates with high affinity which are useful to prevent interaction of heparin or related sulfated glycoconjugates with adhesion molecules, growth factors, cells, or heparin dependent enzymes.

It is further an object to provide peptides which have binding constants which are unexpectedly superior to the binding constants of proteins (peptides) which are known in the art.

It is further an object of the present invention to provide peptides which have a high binding affinity to heparin or related sulfated lactoconjugates and which lack a charge (essentially neutral peptides) in order to formulate more advantageous pharmaceutical agents for efficient delivery to the sites of action.

It is a still further object of the present invention to provide peptides having high potency for binding with heparin or related sulfated glycoconjugates in order to allow much smaller amounts of peptide to be effectively administered and thus reduce risk of toxicity and generation of immune responses against the peptides.

DESCRIPTION OF THE PREFERRED EMBODIMENTS

Figure 1:
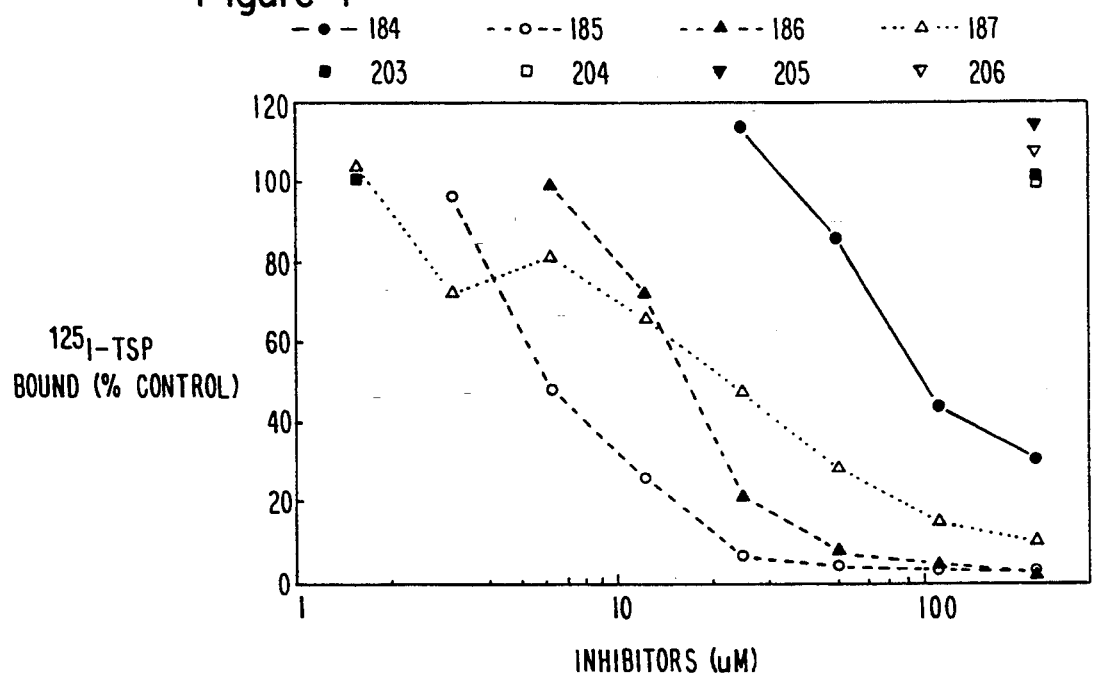
FIG. 1 is a graph illustrating the inhibition of $^{125}$I-thrombospondin binding to sulfated glycoconjugates by thrombospondin peptides.

The present invention provides a peptide having a high binding affinity to heparin or related sulfated glycoconjugates, which is a heparin binding constant in the range of $10^7$ to $10^5$ molar$^{-1}$. Preferred are peptides having a sub-sequence of four or five amino acid residues, which sub-sequence essentially lacks a charge. The term "related sulfated glycoconjugates" as used above and in the application as follows is defined as sulfated glycoconjugates which have binding characteristics similar to heparin. More preferred is a peptide according to the invention having a sequence -Trp-Ser-Xaa-Trp-, wherein -Xaa- is an amino acid selected from the group consisting of Pro, Glu, Ala, His, and Ser. Even more preferred is a peptide according to the invention having a sequence -Trp-Ser-Xaa-Trp- wherein Xaa is defined as described above and further having a sequence selected from the formulae consisting of -B1-B2-X-B3- or -B1-X-B2-Y-B3-, wherein X and Y are independently any amino acid, and B1, B2, and B3 are independently selected from the group consisting of Lys, Arg, and His.

In a particularly preferred embodiment of the invention, the peptide according to the invention described above is a peptide having a sequence independently selected from the group consisting of SEQ ID NO:1, SEQ ID NO:2, SEQ ID NO:3, SEQ ID NO:14, and SEQ ID NO:19.

Further preferred is a peptide having a sequence according to the present invention, wherein said peptide is modified to comprise an amino-terminal N-acetyl and a carboxyl-terminal amide.

The present invention also relates to a pharmaceutical composition comprising an effective amount of a peptide having a high binding affinity to heparin or related sulfated glycoconjugates and essentially lacking a charge, and said composition comprises a pharmaceutically acceptable excipient or carrier.

Even more preferred is a pharmaceutical composition according to the invention, wherein the composition comprises an effective amount of a peptide having a sequence selected from the group consisting of SEQ ID NO:1, SEQ ID NO:2, SEQ ID NO:3, SEQ ID NO:14, and SEQ ID NO:19, in combination with a pharmaceutically acceptable excipient or carrier.

The present invention provides a method for binding heparin or related sulfated glycoconjugates using an effective amount of peptide having a heparin binding constant in the range of $10^7$ to $10^5$ molar$^{-1}$.

Even more preferred is a method wherein the peptide has a sequence selected from the group consisting of SEQ ID NO:1, SEQ ID NO:2, SEQ ID NO:3, SEQ ID NO:14, and SEQ ID NO:19.

BEST MODE FOR CARRYING OUT THE INVENTION

As described above, the present invention provides a family of peptides having high binding affinity to heparin or related sulfated glycoconjugates and essentially lacking a charge. The invention also relates to the use of these peptides to prevent interaction of heparin or related sulfated glycoconjugates with adhesion molecules, growth factors, cells, or heparin-dependent enzymes. More particularly, a preferred peptide according to the present invention is a peptide having a sequence selected from the group consisting of SEQ ID NO:1, SEQ ID NO:2, SEQ ID NO:3, SEQ ID NO:14, and SEQ ID NO:19, which represent a family of related peptides that bind to heparin or related sulfated glycoconjugates with high affinity.

The peptides according to the invention are obtained from the adhesive glycoprotein thrombospondin and described above. The peptides according to the present invention, whose sequences are set forth in Tables 1 and 2, and the sequence listing may be produced by art recognized methods. Such methods include, but are not limited to, peptide production machines, from DNA coding for the peptide inserted in a vector, or by isolating the sequence from the adhisive glycoprotein thrombospondin. Solid phase synthetic methods may also be used. These peptides lack the clusters of basic amino acids which fit the consensus sequences present in many heparin binding proteins and further have binding constants of approximately 10 to 100-fold higher than the proteins having the basic amino acids consensus sequences. The binding constants of the present family of peptides is approximately from $10^7$ to $10^5$ molar$^{-1}$. Further, the substantial lack of an electrical charge for a preferred sub-sequence (having four or five amino acid residues) present in preferred peptides within the family of peptides according to the present invention will be advantageous in formulating pharmaceutical agents based on these peptides for efficient delivery to their sites of action. For certain applications where lack of charge is not required, including use as an adhesive peptide to culture anchorage-dependant cells, modification of the peptide described in the present invention with basic amino acid sequences (such as in SEQ ID NO:19) can increase activity and increase the specificity of the peptide for heparine over other sulfated glycoconjugates.

A further advantage of the present family of peptides is that their higher potency will allow much smaller amounts of peptide to be administered than those required by the prior art peptides and thus will reduce risk of toxicity and generation of immune responses against the peptides.

Peptides from the three type I repeat regions of human thrombospondin were prepared by solid phase synthesis. The peptides used to define heparin binding specificity are listed in Tables 1 and 2 which follow and in the sequence listing accompanying this application. The peptides according to the invention, the pharmaceutical compositions, and the methods according to the invention may be verified using the following general procedures.

The peptides were tested as inhibitors of laminin or thrombospondin binding to a heparin-bovine serum albumen conjugate or to a sulfatide in a solid phase assay essentially following the procedure described in Zabrenetzky et al, Cancer Res., Vol. 50, pages 5937–5942 (1990).

Briefly, heparin-BSA (0.2 μg/well) was absorbed onto polyvinyl chloride microtiter plate wells by incubation in 50 μl of Dulbecco's PBS for 2 h at 37°. The wells were emptied and filled with 50 mM tris, pH 7.8 containing 150 mM NaCl, 0.1 mM CaCl$_2$, 0.1 mM minutes, the wells were emptied and 30 μl of various concentrations of potential inhibitory peptides diluted in the same buffer or buffer alone and 30 μl of $^{125}$I-labeled laminin or thrombospondin (0.2 μg/ml) were added to each well. After 2 hours at 4°, the wells were washed 6 times with 0.15M NaCl, cut from the plate and bound radioactivity counted.

Laminin and thrombospondin binding to sulfatide were determined using a solid phase assay with the glycolipid immobilized in a phosphatidylchlorine/-cholesterol monolayer on polyvinyl chloride microtiter plates.

For inhibition studies of laminin or thrombospondin binding, wells were coated with 200 ng of sulfatide for thrombospondin assays or 600 ng for laminin assays mixed with 50 ng of phosphatidyl choline and 30 ng of cholesterol. The peptides were also tested as inhibitors of melanoma or endothelial cell binding to thrombospondin using centrifugation through oil to separate bound from free ligand.

Figure 2:
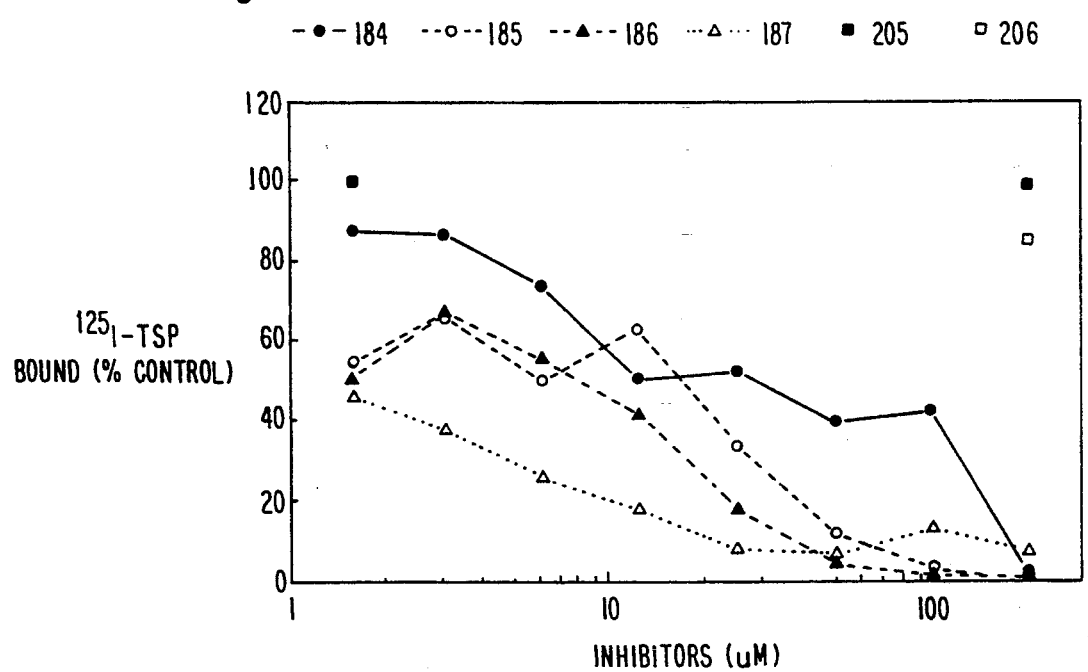
FIG. 2 is a graph illustrating the inhibition of $^{125}$I-thrombospondin binding to sulfated glycoconjugates by thrombospondin peptides.

Several peptides from the type I repeats were tested for inhibition of thrombospondin binding to heparin and sulfatide (FIGS. 1 and 2). The peptides chosen flanked the VTCG sequence (SEQ ID NO:5) identified as an adhesive motif by Rich and coworkers but lacked clusters of basic amino acids needed for the predicted heparin binding consensus sequence. Surprisingly, only the sequences amino-terminal to the VTCG sequence were active (SEQ ID NO:1, SEQ ID NO:2 and SEQ ID NO:3). Dodecapeptides from all three repeats inhibited heparin and sulfatide binding with $I_{50}$ values from 6 to 100 µM (SEQ ID NO:1, SEQ ID NO:2 and SEQ ID NO:3). Flanking peptides adjacent to each active peptide were inactive (SEQ ID NO:6, SEQ ID NO:7 and SEQ ID NO:8). The peptide from repeat 2 (SEQ ID NO:2) was the most followed by repeat 3(SEQ ID NO:3) then repeat 1 (SEQ ID NO:1).

The three repeat peptides were comparable inhibitors of binding to heparin with $I_{50}$ values between 10 and 20 µM. Two peptides from the amino terminal heparin binding domain of thrombospondin containing predicted consensus sequences for heparin binding also inhibited thrombospondin binding to heparin but were much weaker than the type I repeat peptides with $I_{50}$ values greater than 100 µM. These peptides, however, did not inhibit binding to sulfatide.

Figure 3:
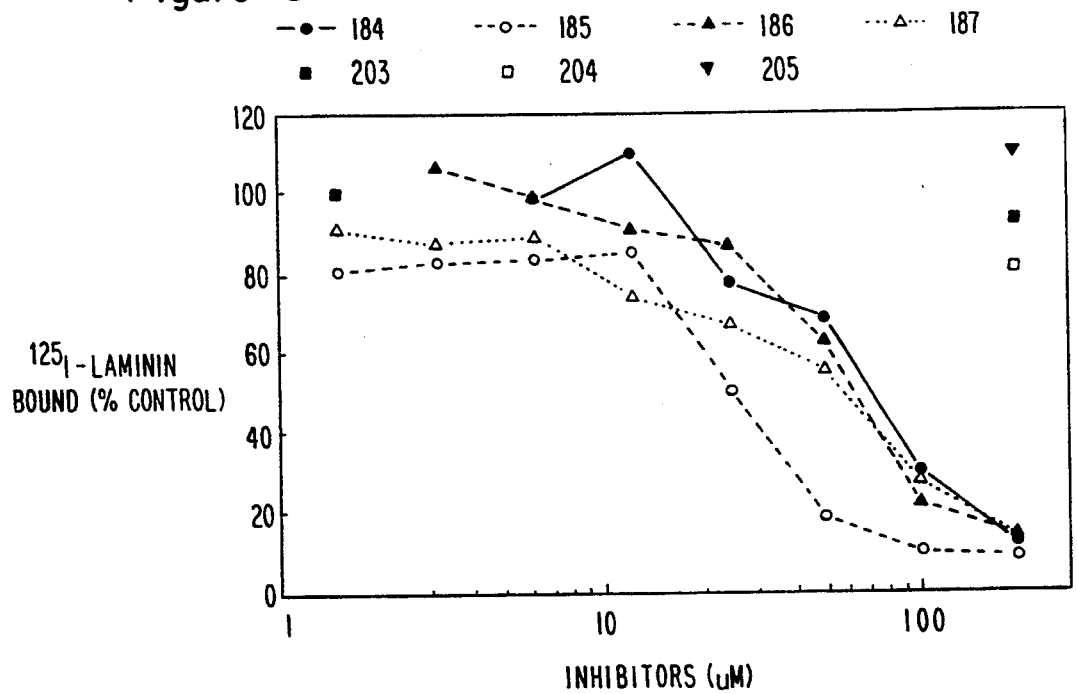
FIG. 3 is a graph showing the inhibition of $^{125}$I-laminin binding to sulfated glycoconjugates by thrombospondin peptides.
Figure 4:
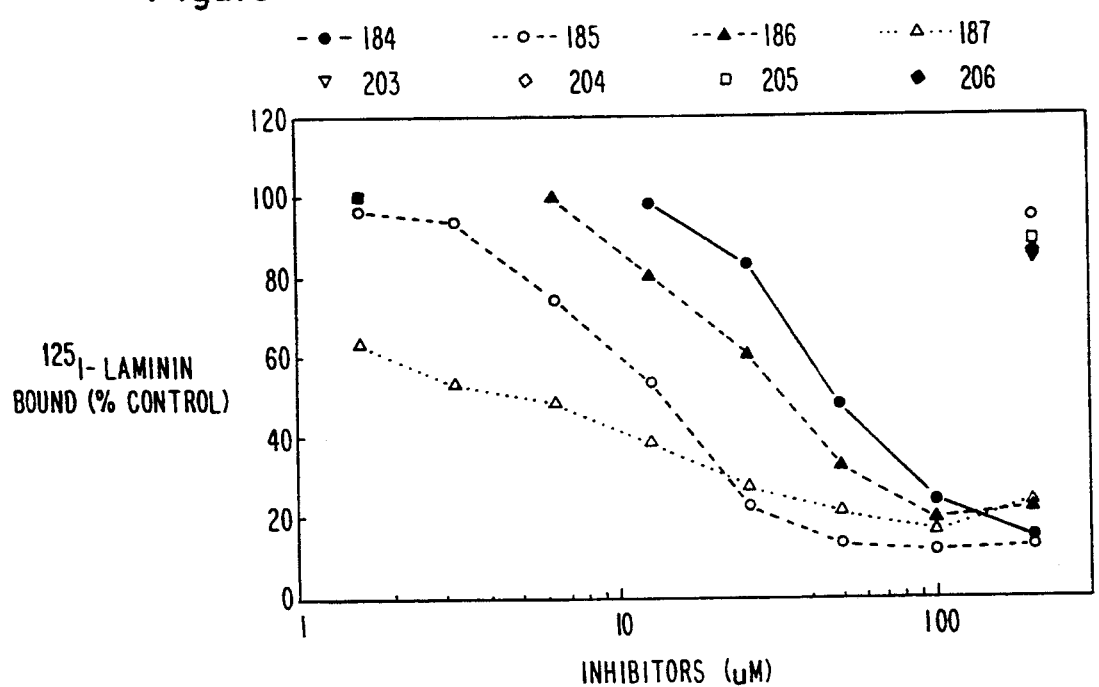
FIG. 4 is a graph showing the inhibition of $^{125}$I-laminin binding to sulfated glycoconjugates by thromospondin peptides.

Since the most active peptides contained few or no basic amino acids, the possibility was considered that the peptides were inhibiting by binding to thrombospondin rather than to the sulfated glycoconjugates. To examine this possibility, the peptides were tested as inhibitors of laminin binding to heparin or sulfatide (FIGS. 3 and 4). The same peptides inhibited laminin binding to both substrates, demonstrating that the activity of the peptides was specific for the sulfated glycoconjugates rather than the protein.

Several peptides containing portions of the most active peptide from the second type I repeat were synthesized to further define the active sequence for heparin binding. VTCG (SEQ ID NO:5) was inactive, although a larger peptide containing this sequence CSVTCG (SEQ ID NO:4) was active. However, this peptide rapidly formed disulfide oligomers in solution and the inhibition curve was much more shallow than the other active peptides suggesting heterogeneous binding or artifactual inhibition secondary to aggregation of the peptide. CSVT (SEQ ID NO:9) was also inactive but addition of two residues to give SSCSVT (SEQ ID NO:13) produced weak inhibition. An eight amino acid peptide from the left part of the second repeat was active (SEQ ID NO:14) as was a ten amino acid peptide lacking only the first two amino acids (SEQ ID NO:16). Substitutionof the two Trp residues in SEQ ID NO:14 with Ala residues (SEQ ID NO:17) abolished activity. Therefore, the Trp residues of SEQ ID NO:14 are required for high affinity binding.

Figure 5:
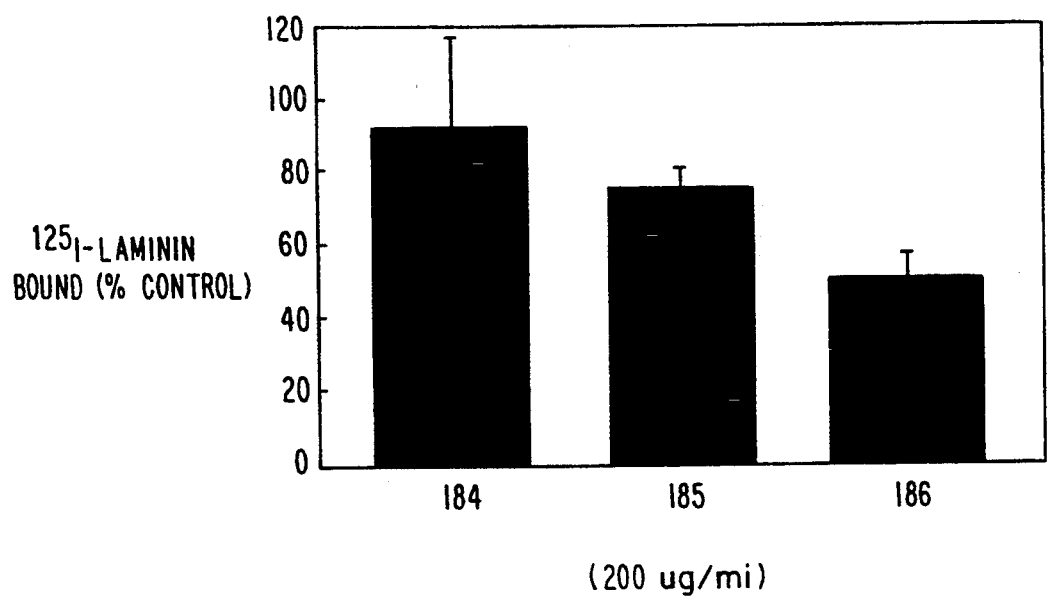
FIG. 5 is a graph representing the inhibition of $^{125}$I-laminin binding to A2058 melanoma cells by thrombospondin peptides.

Effects of peptides on tumor cell binding to thrombospondin or laminin were examined. Peptides from the second and third repeat significantly inhibited laminin binding to A2058 melanoma cells (FIG. 5). As was observed for binding to heparin and sulfatide binding, the peptide from the first repeat was weaker.

Figure 6:
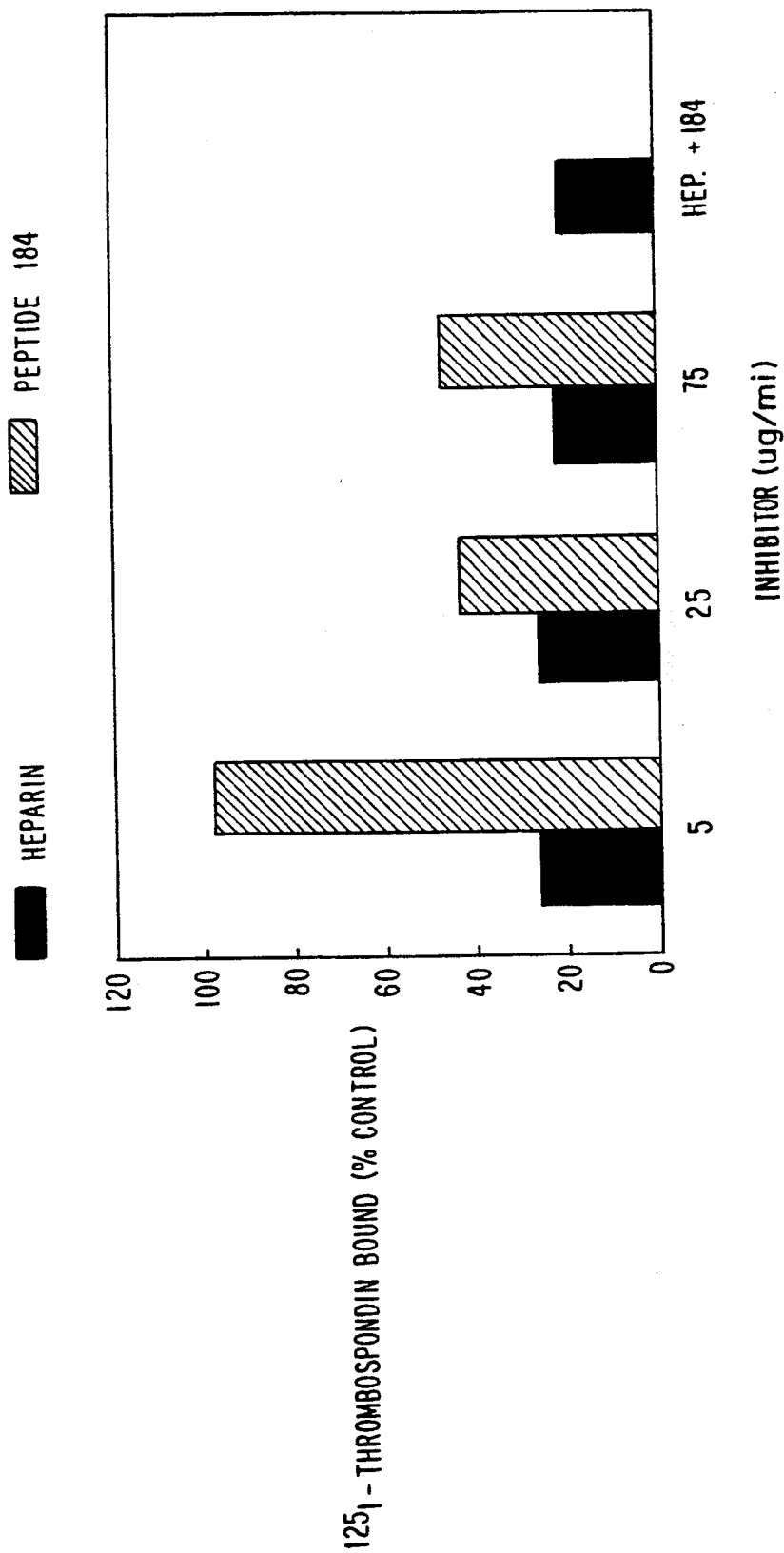
FIG. 6 is a graph representing the inhibition of $^{125}$I-thrombospondin binding to A2058 melanoma cells by heparin and thrombospondin peptide ID SEQ NO:1.

Thrombospondin binding to A2058 melanoma cells was inhibited by peptide 184 (SEQ ID NO:1) from the first repeat (FIG. 6). Inhibition was dose dependent and occurred at comparable concentrations as inhibited thrombospondin binding to heparin or sulfatide. Part of thrombospondin binding to melanoma cells is inhibitable by heparin (FIG. 6). Addition of peptide 184 (SEQ ID NO:1) in the presence of heparin did not further inhibit binding of thrombospondin, indicating that inhibition by the peptide was due to competition with a sulfated glycoconjugate rather than a heparin-resistant protein receptor for thrombospondin on the melanoma cells.

The data demonstrate that a family of peptides from the type I repeats of thrombospondin are potent heparin and sulfatide binding peptides that can inhibit laminin and thrombospondin binding to sulfated glycoconjugates. The peptides are also demonstrated to be inhibitors of heparin-dependent interactions of laminin and thrombospondin with human melanoma cells. Experiments are in progress to determine if these peptides are general inhibitors of heparin-dependent proteins including other adhesive proteins, growth factors, and coagulation enzymes.

Tables 1 and 2, below, list the sequences in a single letter format, which are discussed above and referred to in the figures. The tables list these sequences by a designated peptide number or abreviation and include a corresponding sequence-listing identification number. The sequences are set forth in three-letter peptide code in the sequence listing accompaning this application.

TABLE 1

Inhibition of $^{125}$I-thrombospondin binding to heparin or sulfatide by synthetic peptides.

| Peptides | SEQ ID NO: | Sequences | $I_{50}$ (µM) for binding to: | |
|---|---|---|---|---|
| | | | Heparin | Sulfatide |
| 184 | 1 | S PWSEWTSCSTS | 47 | 14 |
| 186 | 3 | GPWSPWDICSVT | 8.5 | 27 |
| 185 | 2 | SHWSPWSSCSVT | 20 | 5.8 |
| 239 | 14 | SHWSPWSS | 5.2 | 10 |
| 244 | 17 | SHA SPA SS | >200 | >200 |
| 240 | 15 | WSPWSSCS | 60 | ~100 |
| 241 | 16 | WSPWSSCSVT | 35 | 34 |
| 246 | 19 | KRFKQDGGWS HWSPWSS | 2.1 | >100 |

TABLE 1-continued

Inhibition of $^{125}$I-thrombospondin binding to heparin or sulfatide by synthetic peptides.

| Peptides | SEQ ID NO: | Sequences | $I_{50}$ (μM) for binding to: Heparin | Sulfatide |
|---|---|---|---|---|
| 203 | 5 | VTCG | >200 | >200 |
| 204 | 6 | VTCGGGVQKR | >200 | >200 |
| 245 | 18 | VTCGGGVQKRSRL | >200 | >200 |
| 205 | 7 | VTCGDGVITR | >200 | >200 |
| 187 | 4 | CSVTCG | 6 | 14 |
| 237 | 12 | SSVTCG | 58 | 30 |
| 238 | 13 | SSCSVT | 85 | >100 |
| 234 | 9 | CSVT | >200 | >200 |
| 235 | 10 | SSVT | >200 | >200 |
| 236 | 11 | ASVT | >200 | >200 |
| 206 | 8 | TSCGNGIQQR | >200 | >200 |
| P1 | 20 | RQMKKTR | >200 | >200 |
| P2 | 21 | RKGSGRRLVK | 60 | >200 |

TABLE 2

Inhibition of $^{125}$I-laminin or apolipoprotein E binding to heparin or sulfatide by synthetic peptides from the type I repeats of thrombospondin.

| Peptides | SEQ ID NO: | Sequences | Laminin binding to: Heparin | Sulfatide $I_{50}$ (μM) | apoE binding: Heparin |
|---|---|---|---|---|---|
| 184 | 1 | SPWSEWTSCSTS | 36 | 42 | 4.2 |
| 186 | 3 | GPWSPWDICSVT | 15 | 35 | 52 |
| 185 | 2 | SHWSPWSSCSVT | 5 | 15 | 8 |
| 239 | 14 | SHWSPWSS | 11 | 12 | 250 |
| 244 | 17 | SHA SPA SS | >200 | | >200 |
| 240 | 15 | WSPWSSCS | 100 | ~100 | 150 |
| 241 | 16 | WSPWSSCSVT | 34 | 50 | 180 |
| 246 | 19 | KRFKQDGGWS HWSPWSS | 3 | >100 | |
| 203 | 5 | VTCG | >200 | >200 | |
| 245 | 18 | VTCGGGVQKRSRL | ~200 | >200 | |
| 204 | 6 | VTCGGGVQKR | >200 | >200 | |
| 205 | 7 | VTCGDGVITR | >200 | >200 | |
| 187 | 4 | CSVTCG | 3 | 3.9 | 84 |
| 237 | 12 | SSVTCG | 100 | 85 | |
| 234 | 9 | CSVT | >200 | >200 | |
| 235 | 10 | SSVT | >200 | >200 | |
| 236 | 11 | ASVT | >200 | >200 | |
| 238 | 13 | SSCSVT | >200 | >200 | |
| 206 | 8 | TSCGNGIQQR | >200 | | |
| P1 | 20 | RQMKKTR | >200 | >200 | |
| P2 | 21 | RKGSGRRLVK | 60 | >200 | |

DETAILED DESCRIPTION OF FIGS. 1–6

FIGS. 1–6 illustrate data obtained using the above general experimental procedures. The structures (sequences) of the peptides whose data are represented in FIGS. 1–6 are provided in Tables 1 and 2 and by the sequence listing attached to this application.

FIG. 1 is a graph illustrating the inhibition of $^{125}$I-thrombospondin binding to sulfated glycoconjugates by thrombospondin peptides. Microtiter plate wells were coated with sulfatide and incubated with 0.2 μg/ml of labelled thrombospondin in the presence of increasing concentrations of the peptides: SEQ ID NO:1, SEQ ID NO:2, SEQ ID NO:3, SEQ ID NO:4, SEQ ID NO:5, SEQ NO:6, SEQ ID NO:7, and SEQ ID NO:8. At the top of the figure is listed the symbols representing each of the tested peptides which are shown at various concentrations on the graph. Binding is presented as a percent of control binding in the absence of inhibitor.

FIG. 2 is a graph illustrating the inhibition of $^{125}$I-thrombospondin binding to sulfated glycoconjugates by thrombospondin peptides. Microtiter plate wells coated with heparin-BSA sulfatide and incubated with 0.2 μg/ml of labelled thrombospondin in the presence of increasing concentrations of the peptides: SEQ ID NO:1, SEQ ID NO:2, SEQ ID NO:3, SEQ ID NO:4, SEQ ID NO:5, SEQ NO:6, SEQ ID NO:7, and SEQ ID NO:8. At the top of the figure are listed the symbols representing each of the peptide show at various concentrations on the graph. Binding is presented as a percent of control binding in the absence of inhibitor.

FIG. 3 is a graph showing the inhibition of $^{125}$I-laminin binding to sulfated glycoconjugates by thrombospondin peptides. Microtiter plate wells were coated with sulfatide as in FIG. 1, described above. The inhibition due to the particular peptides, listed by symbols and peptide numbers, was also determined as described in FIG. 1.

FIG. 4 is a graph showing the inhibition of $^{125}$I-laminin binding to sulfatated glycoconjugates by thromospondin peptides. Microtiter plate wells were coated with heparin-BSA as described in FIG. 2 above. The inhibition due to the particular peptides, listed by symbols and peptide numbers, was also determined as described in FIG. 2.

FIG. 5 is a graph representing the inhibition of $^{125}$I-laminin binding to A0058 melanoma cells by thrombospondin peptides. Melanoma cells ($1 \times 10^5$ in 0.2 ml) were incubated with 0.2 μg/ml labeled laminin alone or in the presence of 200 micrograms per ml of peptides from SEQ ID NO:1, SEQ ID NO:2, or SEQ ID NO:3, which are the first, second and third repeats from thrombospondin. The cells were centrifuged through oil to separate the free laminin from the bound laminan followed by quantifying the radioactivity in the cell pellett by a gamma counter. The results are presented as a percent of control binding determined in the presence of peptide and is the mean of triplicate determinations ± the standard deviation.

FIG. 6 is a graph representing the inhibition of $^{125}$I-thrombospondin binding to A2058 melanoma cells by heparin and thrombospondin peptide ID SEQ NO:1. Malanoma cells ($3 \times 10^5$ cells in 0.2 ml) were incubated with 0.2 μg/ml of labelled thrombospondin alone or in the presence of increasing concentrations of heparin or peptide having the sequence according to SEQ ID NO:1 or a combination of the two inhibitors. Results are presented as percent of control binding in the absence of inhibitor and are the average of triplicate determination.

DETAILED EXPERIMENTAL PROCEDURE

Materials

Thrombospondin was purified from thrombin-stimulated human platelets as previously described (Roberts et al, J. Biol. Chem. 260, 9405–9411 (1985)). Recombinant heparin-binding fragments of thrombospondin, residues 1–175 ((28kD), and recombinant apolipoprotein E were provided by Biotechnology General, Ltd, Rehovot, Israel. Mouse laminin purified from the Engelbreth Holm Swarm tumor was provided by Dr. Lance Liotta, National Cancer Institute. Monoclonal antibodies to thrombospondin were provided by Dr. William Frazier (Washington University, St. Louis). Thrombospondin, its fragments, apolipoprotein E, BSA-peptide conjugates, and laminin were iodinated using Iodogen (Pierce Chemical Co., Rockford, Ill.) as previously described (Roberts et al, J. Biol. Chem. 260, 9405–9411 (1985)). Heparin-BSA conjugate was prepared by coupling bovine lung heparin (The Upjohn Co.) through the reducing terminus to BSA by reductive emanation in the presence of NaBH$_3$CN essentially as described (Funahashi et al, Anal. Biochem. 126, 414–421 (1982)). Bovine brain sulfatide was obtained from Supelco and dipalmitoylphosphatidylcholine and cholesterol were from Sigma.

Peptides were synthesized corresponding to portions of the three type I repeats of human thrombospondin as indicated in Table 1. Synthesis was done using art recognized methods for peptide synthesis. The peptides used in this study were synthesized on a Biosearch Model 9600 peptide synthesizer using standard Merrifield solid phase synthesis protocols and t-Boo chemistry. Peptides were analyzed by reverse-phase HPLC chromatography. Peptide solutions were neutralized by addition of dilute NaOH and stored in solution at −20°. Peptides were coupled through their cysteine residues to BSA using SPDP (Danilov et al, Exp. Cell Res. 182, 186–196 (1989)).

Adhesion Assays

Human melanoma cell line A2058 (Todaro et al, Proc. Natl. Acad. Sci USA 77, 5258–5262 (1980)) was maintained by monolayer culture at 37° with 5% carbon dioxide in RPMI 1640 medium containing 10% fetal bovine serum. For attachment assays, cells were removed using trypsin, passaged at $10^4$ cells/cm$^2$ and harvested between days 5 and 7. Attachment and spreading on thrombospondin-coated plastic was determined as previously described (Roberts et al, J. Cell Biol. 104, 131–139 (1987)). inhibition was determined by adding the inhibitor diluted in 0.4 ml of bicarbonate-free RPMI 1640 medium, containing 1 mg/ml of bovine serum albumin (fatty acid free, Sigma), pH 7.3, to wells of a 24-well dish containing polystyrene disks coated with proteins or peptides. Melanoma cells were harvested by incubation with phosphate buffered saline containing 2.5 mM EDTA for 20 minutes at 37°. The cells were centrifuged and viability (routinely >99%) was assessed by tripan blue exclusion. The cells were resuspended in medium and allowed to recover in suspension for 1 h. Melanoma cells ($2 \times 10^5$) suspended in 100 μl of medium were added to each well and allowed to attach for 50 to 75 minutes at 37° in a humidified atmosphere. Attachment and spreading were determined microscopically.

Sulfatide and Heparin Binding

Laminin, apolipoprotein E, and thrombospondin binding to sulfatide or heparin were determined using a solid phase assay as previously described (8, 22). Sulfatide (0.2 μg/well for thrombospondin binding, 0.6 μg/well for laminin binding) was immobilized in a mixture of 50 ng of phosphatidyl choline, and 30 ng of cholesterol on polyvinyl chloride microtiter plates. Heparin-BSA (0.2 μg/well) was absorbed onto polyvinyl chloride microtiter plate wells by incubation of 50 μl of Dulbecco's PBS for 2 h at 37°. The wells were emptied and filled with 50 mM tris, pH 7.8 containing 150 mM NaCl, 1 mM CaCl$_2$, 12, 0.025% NaN$_3$, and 1% BSA. After 30 minutes, the wells were emptied and 30 μl of various concentrations of potential inhibitory peptides diluted in the same buffer or buffer alone and 30 μl of $^{125}$I-labeled laminin or thrombospondin (0.2 μg/ml) were added to each well After 3 hours at 4°, the wells were washed 6 times with 0.15M NaCl, cut from the plate and the bound radioactivity counted.

Antibody Binding to Peptides

Inhibition of $^{125}$I-thrombospondin or Laminin Binding to Cells

A2058 melanoma cells were harvested as described above and suspended in Dulbecco's PBS containing 1 mg/ml BSA. In a final volume of 0.2 ml, $2 \times 10^5$ cells were preincubated for 15 minutes with potential inhibitors. Labeled protein was added and incubated on a rotating table for 1 h at 20°. The cell suspension was transferred to 0.4 ml polypropylene microfuge tubes (PGC) which were preincubated with tris BSA buffer. Oil (Nyosil-50, 0.2 ml) was added and centrifuged for 1 min at 10,000 rpm in a Beckman microcentrifuge B. The upper phase was removed and the oil layer was washed with 0.2 ml tris BSA buffer and recentrifuged. The supernatant fluid was aspirated, and the bottom of the tube was cut and counted.

Results

Monoclonal antibody A4.1 binds to a 50 kDa fragment of thrombospondin (Prater et al, J. Cell Biol. 112, 1031–1040 (1991)) which contains the type I repeats that are conserved in several proteins including the circumsporozoite protein of Plasmodium falciparum. In a preliminary screening of thrombospondin antibody reactivity of antibody A4.1 with overlapping peptides from the circumsporozoite protein, we found that antibody A4.1 bound strongly to peptides containing the sequence SISTEWS (M. Seguin and D. Roberts, unpublished results). We therefore prepared peptides from the three type I repeats of thrombospondin homologous to this sequence (Table 1) and tested their binding to antibody A4.1 after conjugation to BSA (FIG. 1). Antibody A4.1 bound strongly to peptide 184 (SEQ IF NO:1) from the first type I repeat and weakly to peptides 185 and 186 (SEQ ID NO:2 and SEQ ID NO:3) from the second and third repeats but not to a series of peptides containing flanking sequences adjacent to the active sequences. Using peptides directly coated on plastic, antibody A4.1 bound best to the peptide 185 (SEQ ID NO:2) from the second repeat and less to the peptides from the first and third repeats (data not shown). Thus, antibody A4.1 binds specifically to three dodecapeptides (12 amino acids in each chain) from the type I repeats of thrombospondin, although it is not clear from the present results whether the antibody distinguishes between the three repeats.

Because adhesion of cells on the 50-50 kD fragment of thrombospondin is partially inhibited by sulfated polysaccharides (Prater et al, J. Cell Biol. 112, 1031-1040 (1991)), several peptides from the type I repeats were tested for inhibition of thrombospondin binding to heparin and sulfatide (FIG. 2A and 2B). The peptides chosen flanked the VTCG sequence (SEQ ID NO:5) identified as an adhesive motif by Rich and co-workers (Rich et al, Science 249, 1574–1577 (1990)), but in most cases lacked clusters of basic amino acids needed for the predicted heparin binding consensus sequence. Surprisingly, the sequences amino-terminal to the VTCG sequence were most active. Dodecapeptides from all three repeats (SEQ ID NO:1, SEQ ID NO:2 and SEQ ID NO:30) inhibited thrombospondin binding to both heparin and sulfatide with $I_{50}$ values ranging from 6 to 50 $\mu$M. The peptide from the third repeat (SEQ ID NO:3) was the most active inhibitor of heparin binding followed by the second and first (SEQ ID NO:1) repeats. The order of inhibition was different for thrombospondin binding to sulfatide, where the second repeat peptide 9SEQ ID NO:2) was the most potent inhibitor (FIG. 2B). Two peptides from the amino terminal heparin binding domain of thrombospondin were tested which contain consensus sequences for heparin binding, resides 23 to 32 and 77 to 83 respectively (Table 1). Only the former peptide inhibited thrombospondin binding to heparin, with an $I_{50}$ value of 60 $\mu$M. These peptides, however, did not inhibit thrombospondin binding to sulfatide.

Since the most active peptides contained few or no basic amino acids, the possibility existed that the peptides were inhibiting by binding to a heparin binding site on thrombospondin rather than to the sulfated glycoconjugates. To examine this hypothesis, the peptides were tested as inhibitors of laminin and apolipoprotein E binding to heparin or sulfatide (FIG. 2C and Table 2). The same peptides were active as inhibitors of both proteins and inhibited laminin binding to both substrates. Since it is highly unlikely that the same peptides could bind specifically to heparin binding sites on three unrelated proteins, the activity of the peptides is due to binding to the sulfated glycoconjugates rather than the protein. Lack of binding of the peptides to laminin or thrombospondin was confirmed by the failure of labeled thrombospondin or laminin to bind to the peptides immobilized directly on plastic or as BSA conjugates (results not shown).

Several peptides containing portions of the most active sequence from the second type I repeat were synthesized and tested as inhibitors of thrombospondin and laminin binding to further define the active sequence for heparin binding (Tables 1 and 2). VTCG was inactive, although a larger peptide containing this sequence, CSVTCG, was active. However, this peptide rapidly formed disulfide oligomers in solution, based on reversed phase HPLC analysis. The inhibition curve was must more shallow than those for the other active peptides (FIG. 2C), suggesting heterogeneous binding or that inhibition may be an artifact due to aggregation of the peptide. An analog of this peptide were the first cysteine was replaced with a serine, SSVTCG, was a very weak inhibitor, except of thrombospondin binding to sulfatide where it was 2-fold less active than CSVTCG. CSVT was also inactive, but addition of two residues on the amino terminus to give SSCSVT produced weak inhibition of thrombospondin binding.

Several smaller peptides derived from the active sequence of the second type I repeat were also potent inhibitors (Tables 1 and 2). The peptide containing the first eight residues, SHWSPWSS, was more active than the intact dodecapeptide for inhibiting thrombospondin binding. A decapeptide lacking the first two amino acids of the dodecapeptide was also a potent inhibitor, but a peptide comprising the center eight residues was much less active. By comparison with the sequences in the other two type I repeats, a minimal consensus sequence for binding may be defined: SXWSPWXS. The two Trp residues and the second Ser residue were entirely conserved. To test the function of tryptophan in binding, an octapeptide was synthesized where the Trp residues were substituted with Ala, SHASPASS. This peptide was more than 100-fold less active than the natural sequence in thrombospondin, SHWSPWSS. Thus, at least one of the two Trp residues is essential for activity.

The putative heparin binding consensus sequence to the right of the VTCG sequence in the third repeat and a similar sequence to the left of the active sequence in the second repeat were also tested for activity (Tables 1 and 2). A peptide containing VTCGY and extending through the BBXB motif (VTCGGGVOKRSRL) was inactive. Addition of the flanking BBXB motif to the second repeat (KRFKQDGGWSHWSPWSS) (SEQ ID NO:19), however, enhanced activity approximately 3-fold for inhibiting thrombospondin or laminin binding to heparin but markedly decreased activity for inhibiting binding of both proteins to sulfatide.

The role of the third Trp residue, the conserved Set residue, and the spacting between the Trp residues in heparin binding activity was examined using synthetic analogs of the type I concensus sequence (See Table 3, below). Addition of a third Trp residue (peptide 256, SEQ ID NO:22) increased activity for laminin binding but decreased activity for thrombospondin slightly. Spacing of the two required T4rp residues three residues apart was critical for aptimum activity as removal of both residues between the two Trp residues abolished activity (peptide 257, SEQ ID NO:23), and the analog with only one residue between the Trp residues (peptide 258, SEQ ID NO:24) was active only for inhibiting laminin binding. Increasing the spacing to four residues (peptide 260, SEQ ID NO:26) or 6 residues (peptide 259, SEQ ID NO:25) also abolished activity. Substitution of the concerved Set residue also caused loss of activity (peptide 261, SEQ ID NO:27). Therefore, at least two Trp residues spaced three residues apart are required for strong activity. The first spacing residue must be Ser, but the second spacing residue is not concerved.

TABLE 3

Inhibition of $^{125}$I-laminin or $^{125}$I-thrombospondin binding to heparin by synthetic peptides from the type I concensus sequence

|  |  |  | Inhibition of: | |
|---|---|---|---|---|
|  |  |  | Thrombospondin binding to Heparin | Laminin binding to Heparin |
| Peptides | SEQ ID NO: |  | | |
|  |  |  | $I_{50}$ (μM) | |
| 256 | 22 | GGWSHWSPWSS | 40 | 3 |
| 257 | 23 | SHWWSS | >400 | 350 |
| 258 | 24 | SHWSWSS | >400 | 30 |
| 259 | 25 | GGWSHASPWSS | >200 | |
| 260 | 26 | SHWSSPWSS | >200 | |
| 261 | 27 | SHWAPWSS | >200 | |

To directly demonstrate binding of the active peptides to heparin, the peptide from the second repeat, 246 (SEQ ID NO:19), was applied to a heparin affinity column (FIG. 3). The peptide was quantitatively bound when applied in tris buffer and eluted on a NaCl gradient in three experiments at 0.13 to 0.16M NaCl. The small unbound peak is a nonpeptide contaminant.

Peptides from the type I repeats significantly inhibited thrombospondin and laminin binding to A2058 melanoma cells (FIG. 4). The order to activities for the peptides was the same as was observed for binding of the respective proteins to heparin. The peptide containing the extended second repeat (246 (SEQ ID NO:19)) was most active, inhibiting thrombospondin binding more than 90% at 10 μg/ml. At the concentrations used, inhibition of binding to melanoma cells by the dodecapeptides from all three type I repeats was partial. In additional experiments (data not shown), inhibition was dose dependent and occurred at comparable concentrations to those needed to inhibit binding of the proteins to heparin. However, complete inhibition could not be demonstrated for the dodecapeptides because binding was enhanced by higher concentrations (results not shown).

Heparin inhibited both thrombospondin and laminin binding to the A2058 melanoma cells (FIG. 4). Thrombospondin binding was inhibited approximately 90%, but approximately 50% of laminin binding was resistant to inhibition by excess heparin. Laminin binding to A20-58 melanoma cells was shown previously to be partially heparin dependent (Taroboletti et al, J. Biol. Chem. 265, 12253–12258 (1990)). Addition of 1 μg/ml peptide 246 in the presence of heparin did not further inhibit binding of laminin (FIG. 5), indicating that inhibition by the peptide was due to competition for binding to a sulfated glycoconjugate rather than to a heparin-resistant protein receptor for laminin on the melanoma cells. At 10 μg/ml of peptide, the inhibition of laminin binding was partially reversed by addition of heparin, probably due to binding of the heparin to the peptide.

Several of the peptides when adsorbed on plastic strongly promoted melanoma cell adhesion (FIG. 6). Activity in the adhesion assay was consistent with the ability of the peptides to inhibit thrombospondin binding to heparin or sulfatide. Peptide 185 (SEQ ID NO:2) was more active than 184 (SEQ ID NO:1) or 186 (SEQ ID NO:3) in both assays. The active subfragments of 185 (SEQ ID NO:4) also promoted cell adhesion. None of the peptides containing VTCG promoted significant cell adhesion above background except CSVTCG (SEQ ID NO:4). As was observed for inhibition of heparin binding substitution of the first Cys residue in CSVTCG (SEQ ID NO:4) with Ser abolished activity in promoting melanoma cell adhesion (SEQ ID NO:2). The two peptides from the amino terminal domain of thrombospondin did not promote melanoma cell adhesion.

Figure 7:
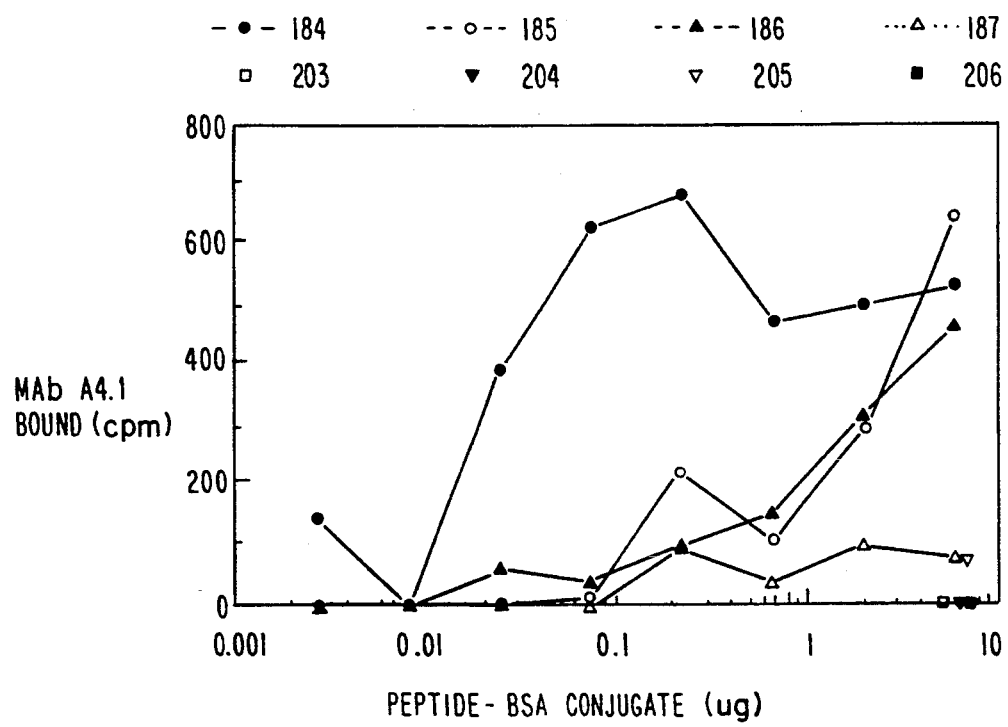
FIG. 7 is a graph representing the binding of anti-thrombospondin antibody A4.1 to thrombospondin peptides.

Adhesion to the peptides was dose dependent (FIG. 7). The extended peptide from the second repeat (246) was most active and, at 10 μg/ml, promoted extensive spreading of melanoma cells. Trp residues were required for adhesion, as the octapeptide containing Ala replacements was inactive.

An 18 kD recombinant heparin-binding fragment of thrombospondin and apolipoprotein E inhibited adhesion of A2058 melanoma cells to the peptides (FIG. 7). Inhibition was greater by apolipoprotein E than by the thrombospondin fragment. This order of activity is consistent with the greater affinity of apolipoprotein E for heparin. Because both proteins bind to heparin sulfate, this result suggests that the peptides are promoting cell adhesion by binding to heparin sulfate proteoglycans on the melanoma cells.

The present invention defines a new class of potent heparin binding peptides from the type I repeat sequences of thrombospondin that lack the currently known heparin binding consensus sequences. The present data demonstrate that peptides from the type I repeats are potent heparin and sulfatide binding peptides that can inhibit interactions of three heparin binding proteins with sulfated glycoconjugates. These peptides may be general inhibitors of heparin-dependent adhesive proteins, growth factors, and coagulation enzymes. The peptides that inhibit binding to heparin strongly promote melanoma cell adhesion when immobilized on plastic. The peptides also inhibit some heparin-dependent interactions of lamino and thrombospondin with human melanoma cells. Although putative heparin binding sequences in the amino terminal domain of thrombospondin are not conserved in the recently identified second gene for thrombospondin (Bornstein et al, J. Biol. Chem. 266, 12821–12824 91991)), the heparin binding sequences from the type I repeats identified here are conserved.

The primary inhibitory activity resides in an octapeptide sequence in each type I repeat that generally lacks basic amino acids but contain two conserved Trp residues and one conserved Ser residue. Substitution with Ala demonstrates that at least one of the Trp residues and the Ser residue are essential for heparin or sulfatide binding and for promoting melanoma cell adhesion. The weak activity of SSCSVT (SEQ ID NO:13) and the enhanced activity of WSPWSSCSVT (SEQ ID NO:16) versus WSPWSSCS (SEQ ID NO:15) suggests that a second active sequence may be present. However, the tetrapeptides CSVT (SEQ ID NO:9) or the previously described VTCG (SEQ ID NO:5) are inactive. The peptide CSVTCG (SEQ ID NO:4) is active. Its activity may require disulfide mediated polymerization, however, since substitution of the first Cys with Ser to prevent polymerization eliminates most activity. It remains to be determined whether two subsites are present or whether the differences in activity of the peptides are due to variation in conformation of a single active sequence among the peptides. VTCG (SEQ ID NO:5) is proposed to be a potential adhesive sequence in the type I repeats that binds to protein receptors for thrombospondin (Rich et al, Science 249, 1574–1577 (1990); Prater et al, J. Cell Biol. 112, 1031–1040 (1991)). This sequence does not bind heparin, but the related peptide CSVTCG (SEQ ID NO:4) inhibits thrombospondin binding to heparin. Because CSVTCG (SEQ ID NO:4) also inhibits binding of laminin and apolipoprotein E, however, this peptide is not useful as a specific probe of thrombospondin binding to potential protein receptors recognizing the VTCG (SEQ ID NO:5) sequence.

A minimal consensus sequence of Ser-X-Trp-Ser-Pro-Trp-X-Ser was derived by comparison of the sequences of the most active peptides. The amino acid residues absolutely conserved in this sequence are the two tryptophans and the serine following the first Trp. At least one of the two Trp residues is essential for activity as substitution of both residues with alanine abolished activity. Thus, in contrast to previously defined heparin binding peptides containing clusters of basic amino acid residues (Cardin et al, Arteriosclerosis 9, 21–32 (1989); Jackson et al, Physiol. Rev. 71, 481–539, (1991)), tryptophan is a major determinant for heparin binding to the type I repeats. Tryptophan has been implicated in heparin binding to antithrombin III (Blackburn et al, J. Biol. Chem. 259, 939–941 (1984)). Chemical modification of Trp 49 blocked heparin binding and heparin-enhanced inhibition of thrombin by antithrombin III. Tryptophan was shown by crystallographic analysis to be directly involved in carbohydrate binding to an anticarbohydrate monoclonal antibody (Cygler et al, Science 252, 442–445, (1991)) and was shown to interact with carbohydrates via van der Waals interactions and hydrogen bonding. An analog of tryptophan, serotonin was also reported to specifically bind to sialyl oligosaccharides (Sturgeon et al, Carbohydr. Res. 103, 213–219 (1982)). Further characterization of the interactions of the thrombospondin peptides with heparin, including spectroscopic and crystallographic analysis, will be needed to determine the role of tryptophan in binding and to examine the contribution of other amino acids including the conserved serine.

Although heparin competes for sulfatide binding to laminin and thrombospondin, the type I repeat peptides reveal some differences between heparin and sulfatide binding activities. The previously defined heparin-binding consensus sequences from the amino terminal domain of thrombospondin weakly inhibit heparin binding. A similar sequence in the second type I repeat enhances inhibition of heparin binding when included with the tryptophan-containing heparin binding sequence. Peptides containing the heparin binding motif BBXB (Asx-Asx-Xaa-Asx), however, failed in all cases to interact with sulfatide. In fact, addition of the basic sequence in the second repeat decreased activity in sulfatide binding assays. A heparin binding motif in conjunction with VTCG (SEQ ID NO:5), which was proposed to mediate sulfatide binding by proteins sharing type I repeat homologies (Holt et al, J. Biol. Chem. 264, 12138–12140 (1989)), did not inhibit thrombospondin binding to heparin or sulfatide and weakly inhibited laminin binding only to heparin. These findings are consistent with our previous report that heparin binding consensus sequences in a denatured 30 kD fragment of the A chain of laminin are sufficient for heparin but not for sulfatide binding (Taraboletti et al, J. Biol. Chem. 265, 12253–12258 (1990)).

Thrombospondin contains two potential heparin binding sites. Both direct binding and antibody inhibition indicate that the amino terminal domain is involved in some interactions with sulfated glycoconjugates on cells. Based on the present results, the type I repeats contain strong heparin binding sequences. Interaction of the 50–70 kD fragment of thrombospondin, which contains these sequences, with melanoma cells is partially heparin dependent (Prater et al, J. Cell Biol. 112, 1031–1040 (1991)). However, the larger 140 kD fragment containing the same sequences does not bind to heparin, sulfatide or heparin sulfate (Roberts, Cancer Res. 48, 6785–6793 (1988); Kaesberg et al, J. Clin. Invest. 83, 994–1001 (1989)). Thus, the sequences are cryptic in this fragment. It cannot be established yet whether the sequence is cryptic in the intact protein. To date, however, all reported interactions of intact thrombospondin with sulfated glycoconjugates have been sensitive to antibody A2.5, which binds to the aminoterminal domain.

FIGS. 7–16, which were briefly described above, are now described in detail below.

FIG. 7 is a graph representing the binding of anti-thrombospondin antibody A4.1 to thrombospondin peptides. Binding of anti-thrombospondin antibody A4.1 (5 µg/ml) to thrombospondin type I repeat peptides conjugated to BSA was determined as described in Materials and Methods. Bound radioactivity is presented as a function of mass of peptide-BSA conjugate added: (184); (185); (186); 187; (203); (204); (205); and (206) (SEQ ID NO:1-SEQ ID NO:8, respectively).

Figure 8:
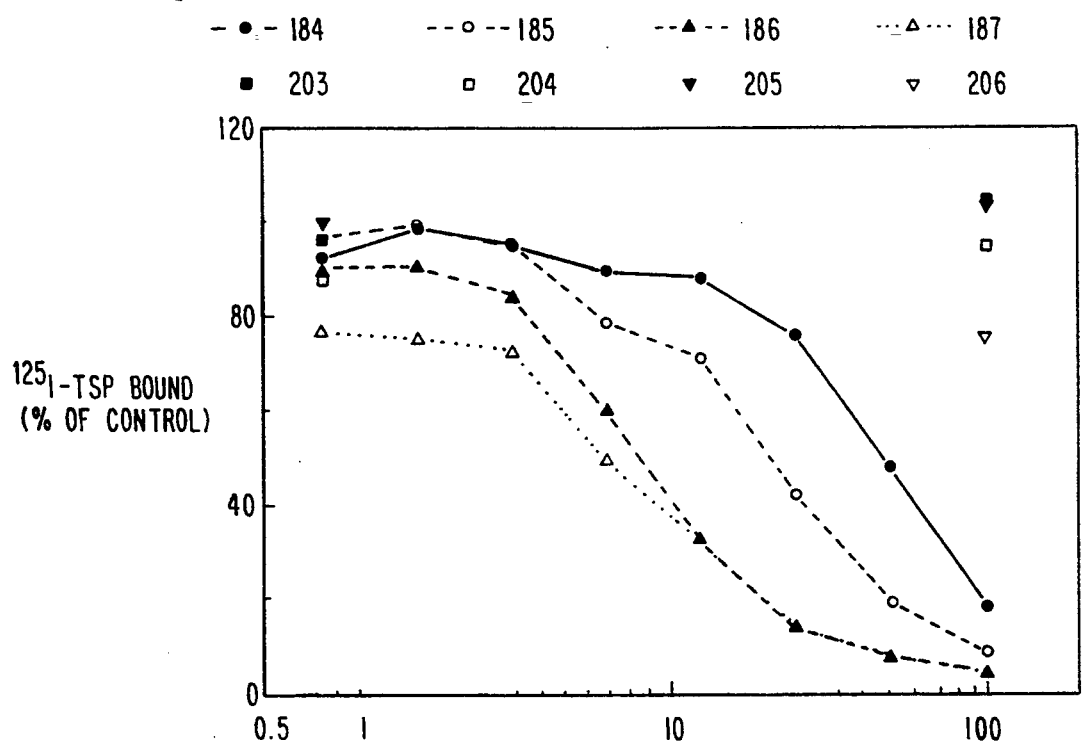
FIG. 8 is a graph representing the inhibition of $^{125}$I-thrombospondin binding to sulfated glycoconjugates (sulfatide) by thrombospondin peptides.

FIG. 8 is a graph representing the inhibition of $^{125}$I-thrombospondin binding to sulfatated glycoconjugates (sulfatide) by thrombospondin peptides. Microtiter plate wells were coated with sulfatide and incubated with 0.2 µg/ml of labelled thrombospondin in the presence of increasing concentrations of the peptides: 184; 185; 186; 187; 203; 204; 205; 206 (SEQ ID NO:1-SEQ ID NO:8, respectively). Structures of the peptides are given in Table 1. Binding is presented as a percent of control binding in the absence of inhibitor.

Figure 9:
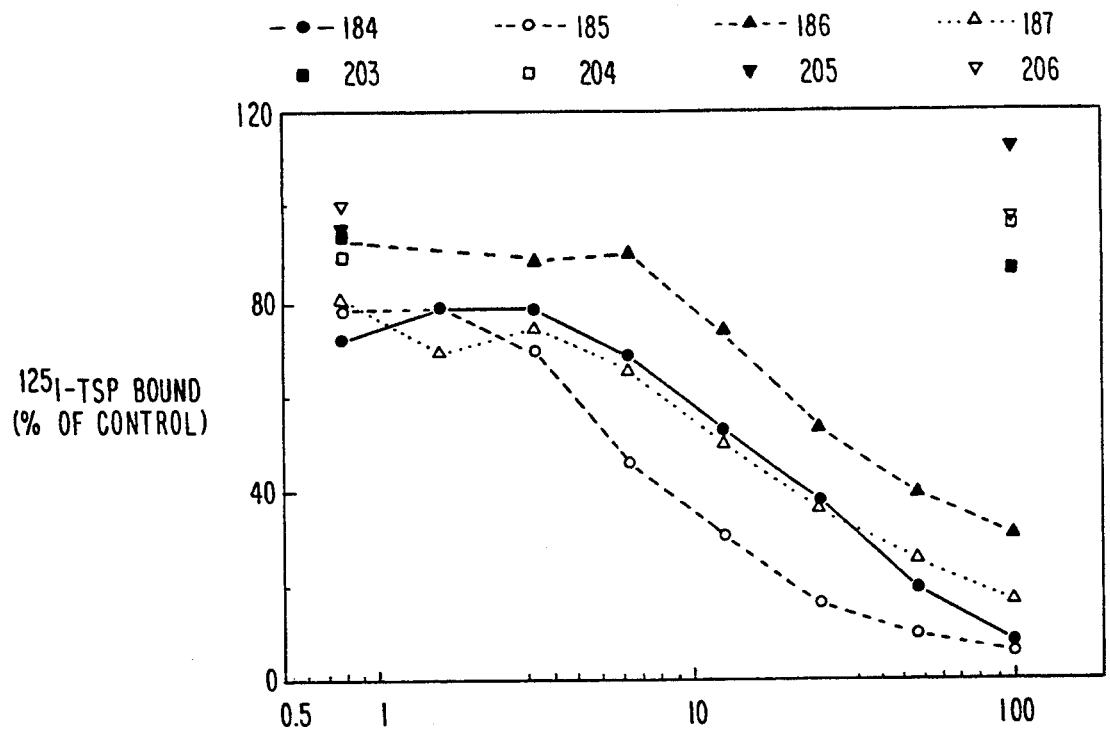
FIG. 9 is a graph representing the inhibition of $^{125}$I-thrombospondin binding to sulfated glycoconjugates (heparin-BSA) by thrombospondin peptides.

FIG. 9 is a graph representing the inhibition of $^{125}$I-thrombospondin binding to sulfatated glycoconjugates (heparin-BSA) by thrombospondin peptides. Microtiter plate wells were coated with heparin-BSA and incubated with 0.2 µg/ml of labelled thrombospondin in the presence of increasing concentrations of the peptides: 184; 185; 186; 187; 203; 204; 205; 206 (SEQ ID NO:1-SEQ ID NO:8, respectively). Structures of the peptides are given in Table 1. Binding is presented as a percent of control binding in the absence of inhibitor.

Figure 10:
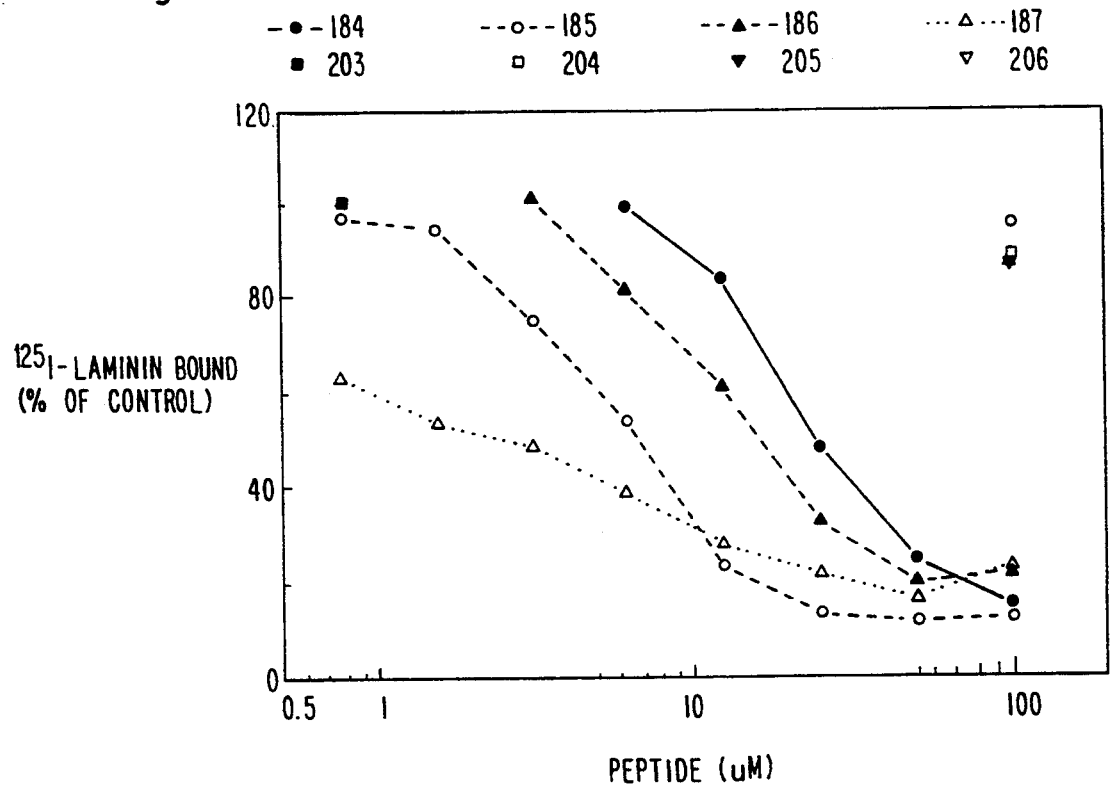
FIG. 10 is a graph representing the inhibition of $^{125}$I-laminin binding to sulfated glyco conjugates (heparin-BSA) by thrombospondin peptides.

FIG. 10 is a graph representing the inhibition of $^{125}$I-laminin binding to sulfatated glyco conjugates (heparin-BSA) by thrombospondin peptides. Microtiter plate wells were coated with heparin-BSA and incubated with 0.2 µg/ml of labelled laminin in the presence of increasing concentrations of the peptides: 184, 185, 186, 187, 203, 204, 205 and 206 (SEQ ID NO:1-SEQ ID NO:8, respectively). Structures of the peptides are given in Tables 1 and 2. Binding is presented as a percent of control binding in the absence of inhibitor.

Figure 11:
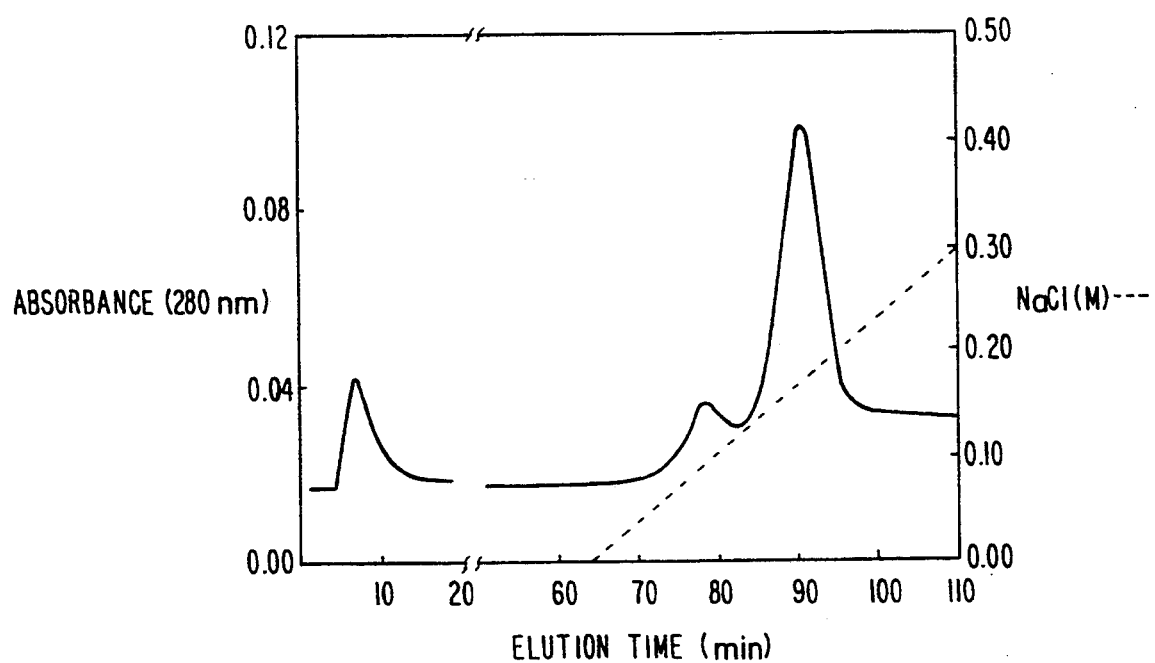
FIG. 11 is a graph showing the binding of a peptide from the second type I repeat of thrombospondin (SEQ ID NO:19) to heparin agarose.

FIG. 11 is a graph showing the binding of a peptide from the second type I repeat of thrombospondin to heparin agarose. Peptide 246 (KRFKQDGGWSHWSPWSS, 100 µg) was applied to a 0.7×7 cm heparin agarose column in 20 mM tris buffer, pH 7.4 and eluted at a flow rate of 0.7 ml/min with a gradient to 0.5M NaCl in the same buffer. Absorbance was monitored at 280 nm. NaCl concentration was determined by conductivity.

Figure 12:
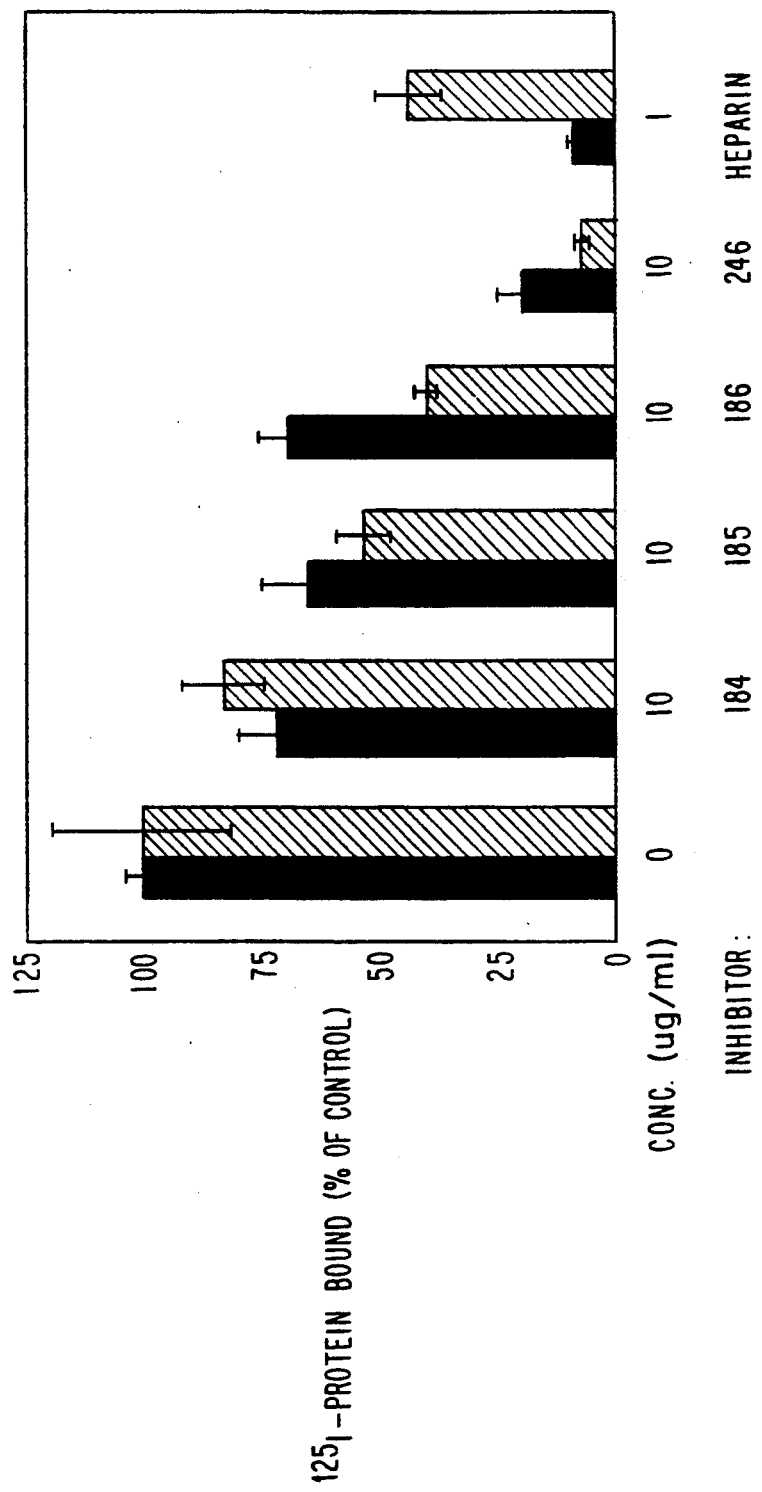
FIG. 12 is a histogram illustrating the inhibition of $^{125}$I-laminin or $^{125}$I-thrombospondin binding to A2058 melanoma cells by thrombospondin peptides.

FIG. 12 is a histogram illustrating the inhibition of $^{125}$I-laminin or $^{125}$I-thrombospondin binding to A2058 melanoma cells by thrombospondin peptides. Melanoma cells ($2\times10^5$ in 0.2 ml) were incubated with 0.2 µg/ml labelled laminin or thrombospondin al one or in the presence of 10 µg/ml of peptides from the first (184, SEQ ID NO:1)), second (185 SEQ ID NO:2) and 246 (SEQ ID NO:19), or third type I repeat of thrombospondin (186) or 1 µg/ml heparin. The cells were centrifuged through oil to separate bound from free laminin and radioactivity in the cell pellet was quantified in a gamma counter. The results are presented as a percent of control binding determined in the absence of peptide and is the mean of triplicate determinations±SD.

Figure 13:
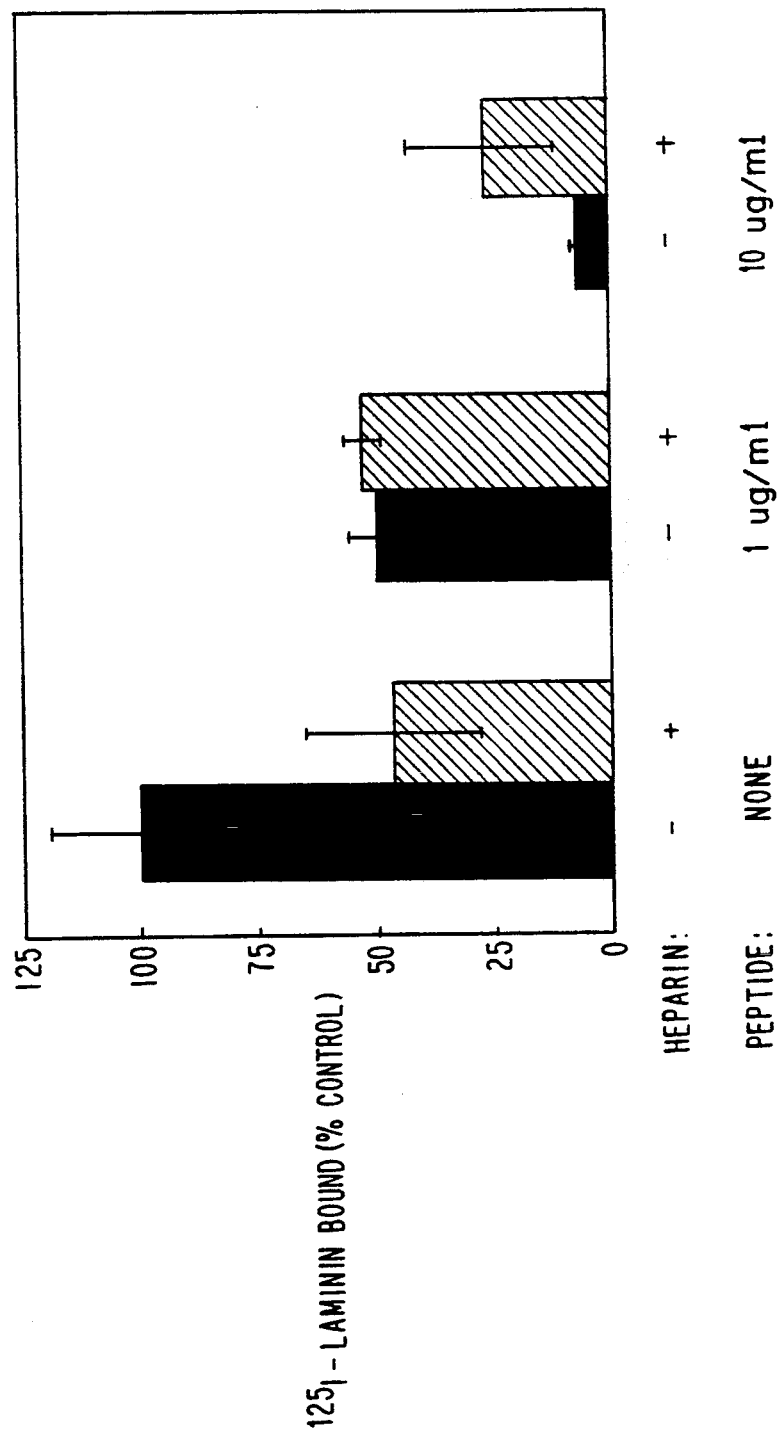
FIG. 13 is a histogram illustrating the inhibition of $^{125}$I-laminin binding to A2058 melanoma cells by heparin and thrombospondin peptide 246 (SEQ ID NO:19).

FIG. 13 is a histogram illustrating the inhibition of $^{125}$I-laminin binding to A2058 melanoma cells by heparin and thrombospondin peptide 246 (SEQ ID NO: 19). Melanoma cells ($2\times10^5$ cells in 0.2 ml) were incubated with 0.2 µg/ml of labelled laminin alone or in the presence of 0.1 µg/ml heparin or 1 or 10 µg/ml peptide 246 or a combination of the two inhibitors. Results are presented as percent of control binding in the absence of inhibitor and are the mean of triplicate determinations±SD.

Figure 14:
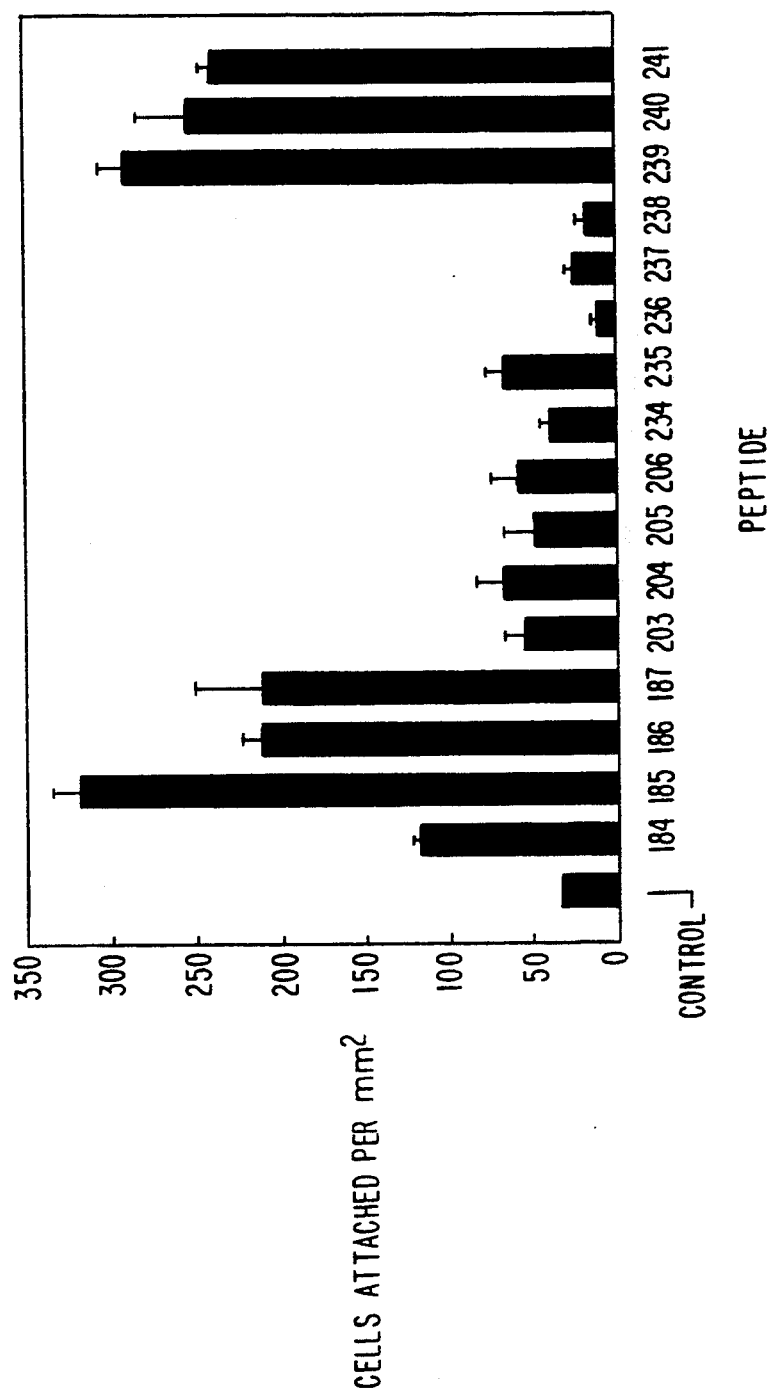
FIG. 14 is a histogram shows the degree of adhesion of A2058 melanoma cells on a control peptide and 16 thrombospondin peptides.

FIG. 14 is a histogram shows the degree of adhesion of A2058 melanoma cells on a control peptide and 16 thrombospondin peptides. Adhesion of A2058 melanoma cells on thrombospondin peptides. Bacteriological polystyrene was coated with the indicated peptides at 200 µg/ml. A2058 melanoma cells, $10^3$/mm$^2$, were added and incubated for 60 min at 37°. Adhesion was determined microscopically and is presented as the mean±SD, n=6.

Figure 15:
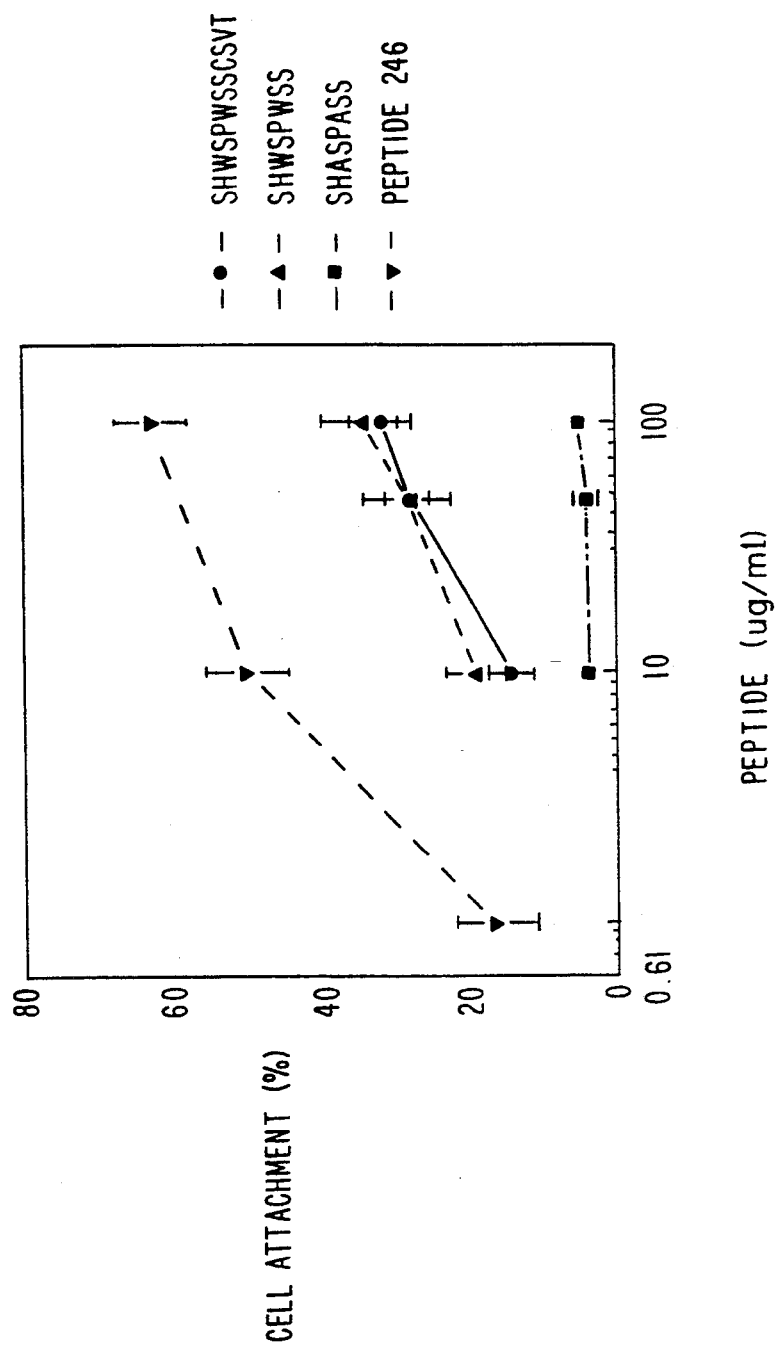
FIG. 15 is a graph showing the concentration dependence for A2058 melanoma cell adhesion to 4 thrombospondin peptides.

FIG. 15 is a graph showing the concentration dependence for A2058 melanoma cell adhesion to 4 thrombospondin peptides. Adhesion determined microscopically is presented as percent of cells applied (mean±SD, n=6) to plastic disks coated with the indicated concentrations of peptides: 185, 239, 244 or 246 (SEQ ID NO: 2, SEQ ID NO: 14, SEQ ID NO: 17, or SEQ ID NO: 19, respectively). Nonspecific adhesion was 1.9±0.9%.

Figure 16:
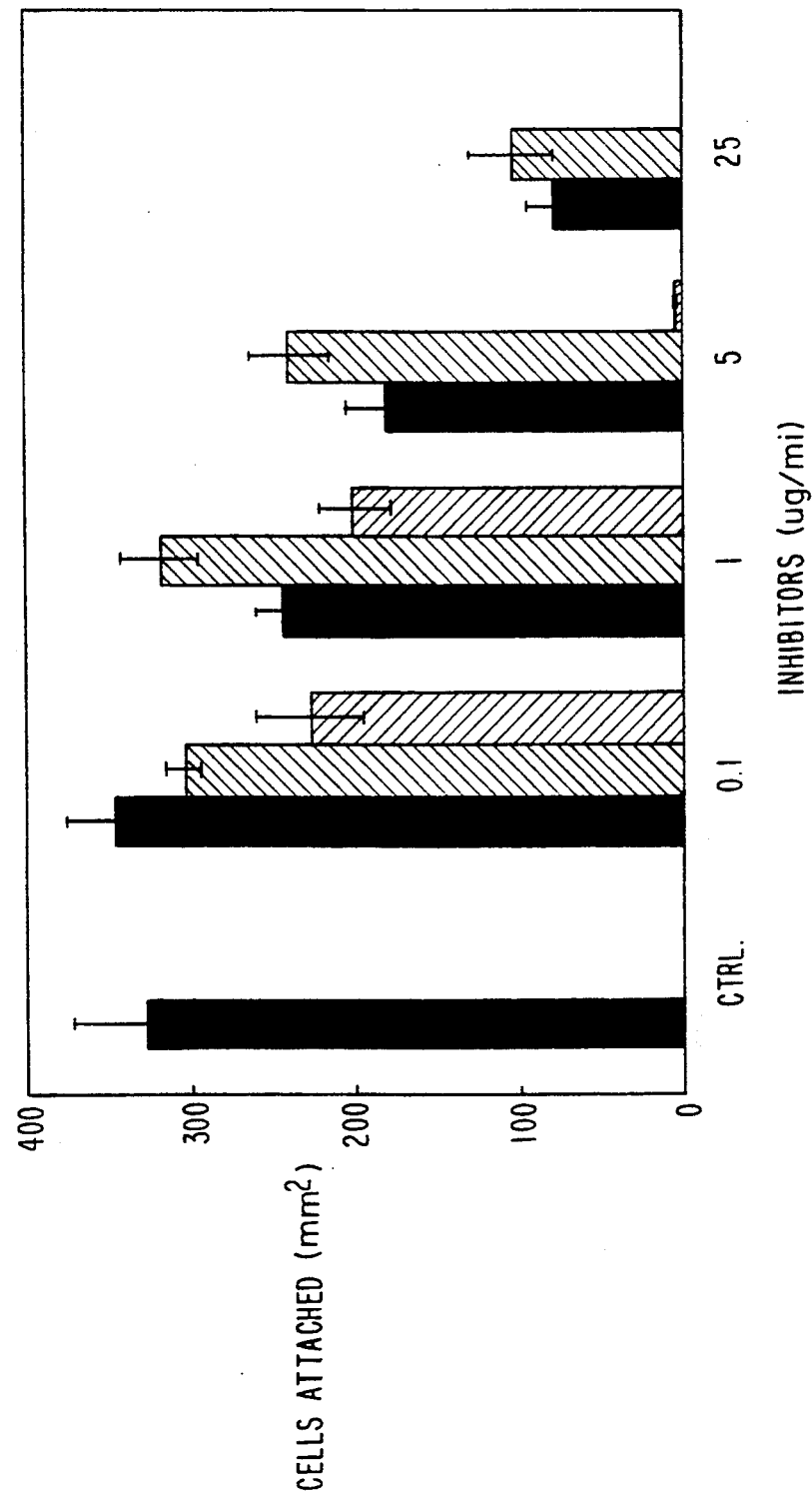
FIG. 16 is a histogram representing the inhibition of melanoma cell adhesion to thrombospondin peptides by heparin binding peptides.

FIG. 16 is a histogram representing the inhibition of melanoma cell adhesion to thrombospondin peptides by heparin binding peptides. Melanoma cells ($1\times10^3$/mm$^2$) in RPMI medium or medium containing the indicated concentrations of 18 kD thrombospondin fragment (solid bars), 28 kD thrombospondin fragment (gray bars), or apolipoprotein E (striped bars) were allowed to attach to polystyrene disks coated with 200 µg/ml peptide 185 (SEQ ID NO:2). Results are presented as mean±SD, n=6.

In another embodiment of the present invention, the peptides according to the present invention may be immobilized on a suitable substrate either directly or after conjugation to a suitable carrier polymer or protein. Suitable substrates, carrier polymers, and carrier proteins are known to one of ordinary skill in the art. Such immobilized compositions are useful to promote adhesion and growth of anchorage-dependent cells. Particularly preferred is an embodiment wherein the immobilized peptide is peptide 246 (SEQ ID NO:19).

The forgoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of a disclosed embodiment. It is to be understood that the phraseology or terminology employed herein is for the purposes of description only and not of limitation.

---

We claim:

1. A synthetic peptide having about 4 to about 17 amino acid residues and consisting essentially of a sequence having a binding affinity for heparin or sulfated glycoconjugates in the range of $10^7$ to $10^5$ molar$^{-1}$, wherein said peptide comprises a subsequence -Trp-Ser-Xaa-Trp-, wherein Xaa- is an amino acid selected from the group consisting of Pro, Glu, Ala, His, and Ser; wherein said subsequence essentially lacks a charge.

2. A synthetic peptide having a sequence selected from the group consisting of SEQ ID NO:1, SEQ ID NO:2, SEQ ID NO:3, SEQ ID NO:14, and SEQ ID NO:19, wherein said sequence has a binding affinity for heparin or sulfated glycoconjugates in the range of $10^7$ to $10^5$ molar$^{-1}$.

3. A composition according to claim 2, wherein said peptide is a peptide having the sequence according to SEQ ID NO:19.

4. A peptide according to claim 2, further comprising an amino-terminal N-acetyl and a carboxyl-terminal amide.

5. A pharmaceutical composition having an effective amount to bind to heparin or sulfated glycoconjugates of a peptide having a sequence selected from the group consisting of SEQ ID NO:1, SEQ ID NO:2, SEQ ID NO:3, SEQ ID NO:14, and SEQ ID NO:19, wherein said sequence has a binding affinity for heparin or sulfated glycoconjugates in the range of $10^7$ to $10^5$ molar$^{-1}$ and a pharmaceutically acceptable excipient or carrier.

6. A pharmaceutical composition according to claim 5, wherein said effective amount of a peptide to bind to heparin or sulfated glycoconjugates is about 6 to about 100 μM concentration.

7. A peptide according to claim 2, optionally conjugated with a suitable carrier polymer or protein, wherein said peptide, or said peptide conjugated with a suitable carrier polymer or protein, is bound to a suitable substrate.

8. A peptide according to claim 7, wherein said suitable carrier polymer or protein is selected from the group consisting of sulfatide and a mixture of phosphatidyl choline and cholesterol, and wherein said suitable substrate is a polyvinylchloride microtiter plate.

9. A method according to claim 7, wherein said suitable substrate is selected from the group consisting of a polyvinylchloride, polystyrene or plastic.

* * * * *

UNITED STATES PATENT AND TRADEMARK OFFICE
CERTIFICATE OF CORRECTION

PATENT NO. : 5,357,041
DATED : October 18, 1994
INVENTOR(S) : David D. ROBERTS et al It is certified that error appears in the above-indentified patent and that said Letters Patent is hereby corrected as shown below:

Column 28, line 63, change "method" to --peptide--.

Signed and Sealed this

Eighteenth Day of July, 1995

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ser Pro Trp Ser Glu Trp Thr Ser Cys Ser Thr Ser
1               5                   10
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ser His Trp Ser Pro Trp Ser Ser Cys Ser Val Thr
1               5                   10
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly Pro Trp Ser Pro Trp Asp Ile Cys Ser Val Thr
1               5                   10
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Cys Ser Val Thr Cys Gly
1               5
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Val Thr Cys Gly
1
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Val Thr Cys Gly Gly Gly Val Gln Lys Arg
1               5                   10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Val Thr Cys Gly Asp Gly Val Ile Thr Arg
1               5                   10
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Thr Ser Cys Gly Asn Gly Ile Gln Gln Arg
1               5                   10

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Cys Ser Val Thr
1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Ser Ser Val Thr
1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Ala Ser Val Thr
1

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Ser Ser Val Thr Cys Gly
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ser Ser Cys Ser Val Thr
1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Ser His Trp Ser Pro Trp Ser Ser
1               5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Trp Ser Pro Trp Ser Ser Cys Ser
1               5
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Trp Ser Pro Trp Ser Ser Cys Ser Val Thr
1               5                   10
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Ser His Ala Ser Pro Ala Ser Ser
1               5
```

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Val Thr Cys Gly Gly Gly Val Gln Lys Arg Ser Arg Leu
1               5                   10
```

( 2 ) INFORMATION FOR SEQ ID NO:19:

( i ) SEQUENCE CHARACTERISTICS:
        ( A ) LENGTH: 17 amino acids
        ( B ) TYPE: amino acid ( D ) TOPOLOGY: linear ( i i ) MOLECULE TYPE: peptide ( x i ) SEQUENCE DESCRIPTION: SEQ ID NO:19:

Lys Arg Phe Lys Gln Asp Gly Gly Trp Ser His Trp Ser Pro Trp Ser
1               5                   10                  15
Ser ( 2 ) INFORMATION FOR SEQ ID NO:20:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Arg Gln Met Lys Lys Thr Arg
1               5

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Arg Lys Gly Ser Gly Arg Arg Leu Val Lys
1               5                   10

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Gly Gly Trp Ser His Trp Ser Pro Trp Ser Ser
1               5                   10

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Ser His Trp Trp Ser Ser
1               5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
      Ser His Trp Ser Trp Ser Ser
      1               5
```

( 2 ) INFORMATION FOR SEQ ID NO:25:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
      Gly Gly Trp Ser His Ala Ser Pro Trp Ser Ser
      1               5                   10
```

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
      Ser His Trp Ser Ser Pro Trp Ser Ser
      1               5
```

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
      Ser His Trp Ala Pro Trp Ser Ser
      1               5
```